US011139561B2

(12) United States Patent
LeBaron et al.

(10) Patent No.: US 11,139,561 B2
(45) Date of Patent: *Oct. 5, 2021

(54) FABRIC ANTENNA

(71) Applicant: Stimwave Technologies Incorporated, Pompano Beach, FL (US)

(72) Inventors: Richard LeBaron, Miami Beach, FL (US); Laura Tyler Perryman, Pompano Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,854

(22) Filed: Jan. 17, 2020

(65) Prior Publication Data
US 2020/0220253 A1 Jul. 9, 2020

Related U.S. Application Data

(63) Continuation of application No. 15/663,300, filed on Jul. 28, 2017, now Pat. No. 10,541,468.
(Continued)

(51) Int. Cl.
*H01Q 1/38* (2006.01)
*H01Q 1/27* (2006.01)
(Continued)

(52) U.S. Cl.
CPC ............ *H01Q 1/273* (2013.01); *G06K 19/067* (2013.01); *H01Q 1/27* (2013.01); *H01Q 1/38* (2013.01);
(Continued)

(58) Field of Classification Search
CPC .......... H01Q 1/273; H01Q 9/26; H01Q 9/285; H01Q 1/38; H01Q 21/062; H01Q 21/06;
(Continued)

(56) References Cited

U.S. PATENT DOCUMENTS 6,028,565 A 2/2000 Mackenzie et al.
6,377,216 B1 4/2002 Cheadle et al.
(Continued)

FOREIGN PATENT DOCUMENTS

WO  WO 2012/103519  8/2012
WO  WO 2012/138782  10/2012
(Continued)

OTHER PUBLICATIONS

International Search Report and Written Opinion in International Application No. PCT/US2017/044489, dated Nov. 24, 2017, 15 pages.
(Continued)

*Primary Examiner* — Hai V Tran
(74) *Attorney, Agent, or Firm* — Fish & Richardson P.C.

(57) ABSTRACT

An antenna assembly includes: a wearable antenna including a conductive signal layer having a radiating surface; a feed conductive layer; and an insulating layer in between the conductive signal layer and the feed conductive layer, and wherein the conductive signal layer, the feed conductive layer, and the insulating layer are fabric-based, wherein the wearable antenna is shaped and sized to be embedded in a subject's clothing with sufficient flexibility to be stretched and bent as the subject implanted with a passive implantable stimulator device maintains routine daily activities, and wherein the wearable antenna is electrically tuned and configured to have the radiating surface of the conductive signal layer facing the subject's skin and a feed point of the feed conductive layer connecting to a controller such that the wearable antenna is non-inductively coupled to the implanted passive stimulator device to supply power the passive implantable stimulator device wirelessly and non-inductively.

20 Claims, 29 Drawing Sheets

Related U.S. Application Data

(60) Provisional application No. 62/367,766, filed on Jul. 28, 2016.

(51) Int. Cl.

| | | |
|---|---|---|
| *H01Q 9/26* | (2006.01) | |
| *H01Q 9/28* | (2006.01) | |
| *H01Q 21/06* | (2006.01) | |
| *G06K 19/067* | (2006.01) | |
| *A61F 13/00* | (2006.01) | |

(52) U.S. Cl.
CPC .............. *H01Q 9/26* (2013.01); *H01Q 9/28* (2013.01); *H01Q 9/285* (2013.01); *H01Q 21/06* (2013.01); *H01Q 21/062* (2013.01); *A61F 13/00051* (2013.01)

(58) Field of Classification Search
CPC .......... H01Q 1/27; H01Q 9/28; G06K 19/067; A61F 13/00051
USPC ........................................................ 343/718
See application file for complete search history.

(56) References Cited

U.S. PATENT DOCUMENTS

| | | | |
|---|---|---|---|
| 9,409,029 B2* | 8/2016 | Perryman | A61N 1/3787 |
| 9,757,571 B2* | 9/2017 | Perryman | A61N 1/37252 |
| 10,541,468 B2 | 1/2020 | LeBaron et al. | |
| 2002/0123289 A1 | 9/2002 | Deangelis et al. | |
| 2003/0192102 A1* | 10/2003 | Marmaropoulos | H01Q 1/273 2/69 |
| 2005/0235482 A1 | 10/2005 | Deaett et al. | |
| 2007/0210973 A1 | 9/2007 | Tanaka et al. | |
| 2008/0160851 A1 | 7/2008 | Dunn et al. | |
| 2009/0295657 A1 | 12/2009 | Gakhar et al. | |
| 2011/0012788 A1 | 1/2011 | Rowell et al. | |
| 2013/0056689 A1 | 3/2013 | Zhang et al. | |
| 2013/0068499 A1* | 3/2013 | Singh | H01F 5/00 174/113 R |
| 2013/0069748 A1* | 3/2013 | Singh | H01F 38/14 336/115 |
| 2013/0093633 A1* | 4/2013 | Henderson | H01Q 1/36 343/718 |
| 2014/0180365 A1* | 6/2014 | Perryman | H01Q 1/273 607/60 |
| 2014/0318699 A1 | 10/2014 | Longinotti-Buitoni | |
| 2015/0321017 A1* | 11/2015 | Perryman | A61N 1/36125 607/61 |
| 2016/0149293 A1 | 5/2016 | Walker | |
| 2016/0165970 A1* | 6/2016 | Jost | H01G 11/24 219/211 |
| 2016/0184597 A1* | 6/2016 | Andresen | A61N 1/37229 607/60 |
| 2016/0190698 A1* | 6/2016 | Andresen | A61N 1/37223 607/60 |
| 2016/0261031 A1* | 9/2016 | Dion | H01Q 1/248 |
| 2017/0018843 A1* | 1/2017 | Kourti | H01Q 9/26 |

FOREIGN PATENT DOCUMENTS

| | | |
|---|---|---|
| WO | WO 2013/019757 | 2/2013 |
| WO | WO 2013/025632 | 2/2013 |
| WO | WO 2013/040549 | 3/2013 |

OTHER PUBLICATIONS

International Preliminary Report on Patentability in International Appln. No. PCT/US2017/044489, dated Jan. 29, 2019, 12 pages.
PCT Invitation to Pay Additional Fees where Applicable in International Appln. No. PCT/US2017/044489, dated Sep. 26, 2017, 2 pages.

* cited by examiner

Antennas currently used in the Fabric Design

Dipole Array Antenna for Subcutaneous Stimulation

Printed Conductive Ink Traces

Dipole Array Antenna Version 2

Band-Aid Antenna

Band-Aid

FABRIC ANTENNA

CROSS-REFERENCE TO RELATED APPLICATION

This application is a continuation of U.S. application Ser. No. 15/663,300, filed Jul. 28, 2017, now allowed, which claims the benefit of U.S. Provisional Application No. 62/367,766, filed Jul. 28, 2016, and titled "FABRIC ANTENNA." Both of these prior applications are incorporated by reference in their entirety.

TECHNICAL FIELD

This application generally relates to a RF stimulation system including an antenna assembly to remotely provide power and stimulation parameters to an implantable device.

BACKGROUND

Antennas have been designed and utilized with implanted devices to aid in the treatment of various medical conditions. Often, these antennas are placed close to the patient's body. In some cases, the conductive element of the antennas would be subject to excessive absorption of electromagnetic energy, which, when these antennas are placed close to the patient's body, could lead to adverse events such as burning of tissue, creation of undesirable blood clots and skin irritation from adherence of the antenna directly to skin tissue.

SUMMARY

In one aspect, some implementations provide an antenna assembly that includes: a wearable antenna that comprises: a conductive signal layer comprising a radiating surface; a feed conductive layer comprising a feed point; and an insulating layer in between the conductive signal layer and the feed conductive layer, and wherein the conductive signal layer, the feed conductive layer, and the insulating layer are fabric-based, wherein the wearable antenna is shaped and sized to be embedded in a subject's clothing with sufficient flexibility to be stretched and bent as the subject implanted with a passive implantable stimulator device maintains routine daily activities, and wherein the wearable antenna is electrically tuned and configured to have the radiating surface of the conductive signal layer facing the subject's skin and the feed point of the feed conductive layer connecting to a controller such that the wearable antenna is non-inductively coupled to the implanted passive stimulator device to supply power the passive implantable stimulator device wirelessly and non-inductively.

Implementations may include one or more of the following features.

The wearable antenna may include a dipole antenna array in which the conductive signal layer comprises: two or more conductor strips arranged in parallel. The two or more conductor strips may include conductive ink printed on fabric material. The two or more conductor strips may include an upper conductor strip and a lower conductor strip symmetrically shaped to provide rounded corners to the conductive signal layer. The two or more conductor strips may include one or more conductor strips each having a central gap that evenly divides the conductor strip into symmetric halves laterally on both sides relative to the feed point. The feed conductive layer may include an X-shaped conductor trace having a central gap that divides the feed conductive layer into symmetric halves. The feed point may be located at the central gap and configured to connect to the controller device via a coax cable.

The wearable antenna may be characterized by a transmission loss profile that varies no more than 2 dB over a region where the passive implantable stimulator device has been implanted. The wearable antenna may be characterized by a reflection profile in which reflected power remains at least 8 dB lower than an input power over a region where the passive implantable stimulator device has been implanted. The wearable antenna may have a power deposition pattern that varies by less than 33% over an implantation depth of 1 cm. The wearable antenna may be tuned and matched throughout a band of operating frequencies that range from a first frequency of about 300 MHz to a second frequency of about 3 GHz.

The wearable antenna may include a patch antenna. The wearable antenna may be characterized by a transmission loss profile that varies no more than 1 dB over a region where the passive implantable stimulator device has been implanted. The wearable antenna may be characterized by a reflection profile in which reflected power remains at least 20 dB lower than an input power over a region where the passive implantable stimulator device has been implanted. The wearable antenna may have a power deposition pattern that varies by less than 33% over an implantation depth of 1 cm. The wearable antenna may be tuned and matched throughout a band of operating frequencies that range from a first frequency of about 300 MHz to a second frequency of about 3 GHz.

In yet another aspect, some implementations provide an antenna assembly that includes a wearable antenna that includes a band aid antenna with one conductive layer shaped in a band aid form and comprising a central gap that evenly divides the band aid form, and wherein the conductive layer is fabric-based, wherein the wearable antenna is shaped and sized to be embedded in a subject's clothing with sufficient flexibility to be stretched and bent as the subject implanted with a passive implantable stimulator device maintains routine daily activities, and wherein the wearable antenna is electrically tuned and configured to have a radiating surface of the conductive layer facing the subject's skin and a feed point of the conductive layer connecting to a controller such that the wearable antenna is non-inductively coupled to the implanted passive stimulator device to supply power the passive implantable stimulator device wirelessly and non-inductively.

Implementations may include one or more of the following features. The wearable antenna may be characterized by a transmission loss profile that varies no more than 6 dB over a region where the passive implantable stimulator device has been implanted. The wearable antenna may be characterized by a reflection profile in which reflected power remains at least 17 dB lower than an input power over a region where the passive implantable stimulator device has been implanted.

In still another aspect, some implementations provide an antenna assembly that includes a wearable antenna including: a band aid array antenna that comprises more than one band aid bars, each band aid bar having a feed point, each band aid bar comprising a central gap that evenly divides the respective band aid bar, each band aid bar comprising a conductive layer that is fabric-based, and wherein the wearable antenna is shaped and sized to be embedded in a subject's clothing with sufficient flexibility to be stretched and bent as the subject implanted with a passive implantable stimulator device maintains routine daily activities, and wherein the wearable antenna is electrically tuned and configured to have a radiating surface of the conductive layer facing the subject's skin and the feed point of the band aid bar connecting to a controller such that the wearable antenna is non-inductively coupled to the implanted passive stimulator device to supply power the passive implantable stimulator device wirelessly and non-inductively.

Implementations may include one or more of the following features.

The band aid bars may be configured to be operable to form a constructive interference over a region where the passive implantable stimulator device has been implanted. Each feed point of the feed conductive layer may be driven by a voltage input, and wherein the respective voltage input varies in at least one phase factor.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 5A shows an example of a dipole antenna array while

Like reference symbols in the various drawings indicate like elements.

DETAILED DESCRIPTION

Figure 1:
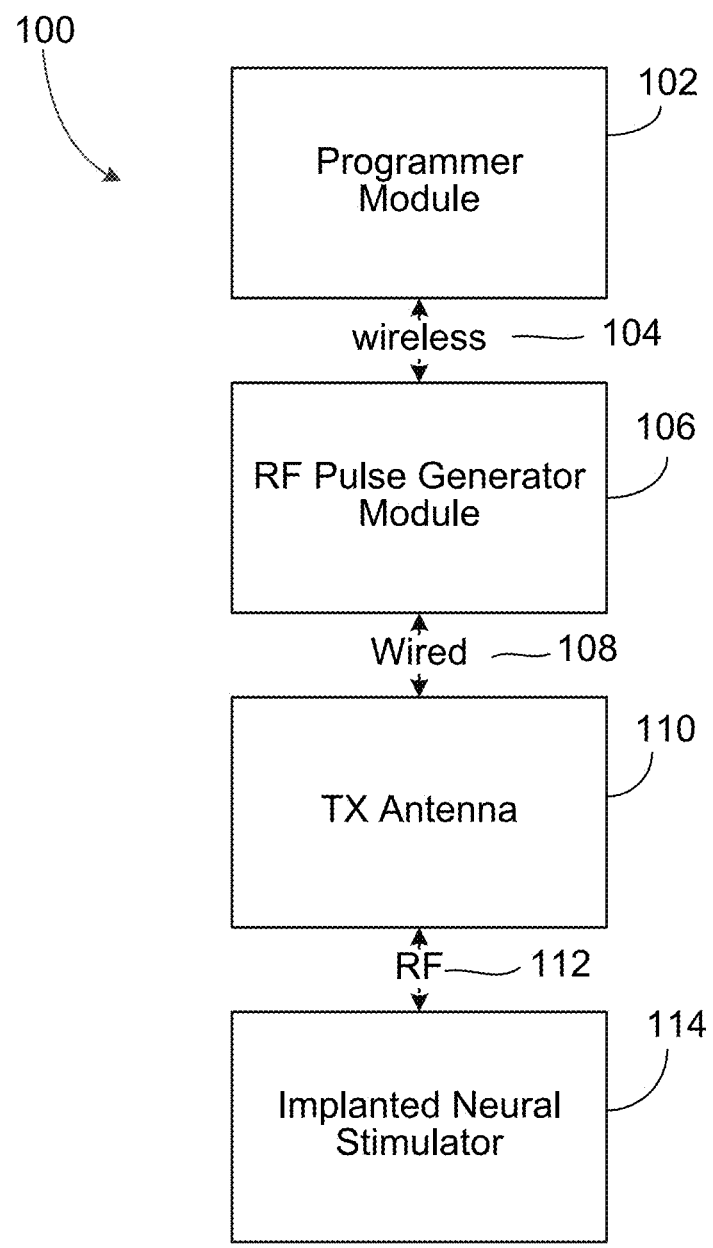
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

Antennas can be designed for the purpose of transmitting microwave energy to a receiving antenna located just below a patient's skin, or on the skin, from a distant location (e.g., of up to four to six feet and stationary). The antenna design may be dependent on the mobility needs of the patient while receiving the therapy. The antenna may advantageously have a minimum profile so that the antenna can blend in with the ambiance of the room. The disclosure focuses on the design of a compact remote transmitting antenna with superior matching and gain, as well as being several orders of magnitude less expensive than comparable antennas and very easy to manufacture.

According to some implementations, a wireless stimulation system can include an antenna assembly coupled to a controller module and configured to radiate electromagnetic energy to an implantable device. In some instances, the implantable device can be a passive neural stimulator device configured to receive RF energy and stimulation parameters wirelessly. Solely by using the received electromagnetic energy, the implantable passive neural stimulator creates one or more stimulation pulses to stimulate neural tissue of a patient. In particular, the antenna assembly can include an antenna with a bowtie-shaped radiating surface and a feed port. The feed port may be coupled to a controller module that drives the antenna to transmit the electromagnetic energy from the bowtie radiating surface. The bowtie shaped radiating surface is generally sized and shaped to radiate the electromagnetic energy to match a reception characteristic of the implantable passive neural stimulator. In one example, the implantable passive neural stimulator includes a dipole antenna and the radiating surface is configured to transmit polarized electromagnetic energy commensurate with dipole reception characteristics.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

Figure 14A:
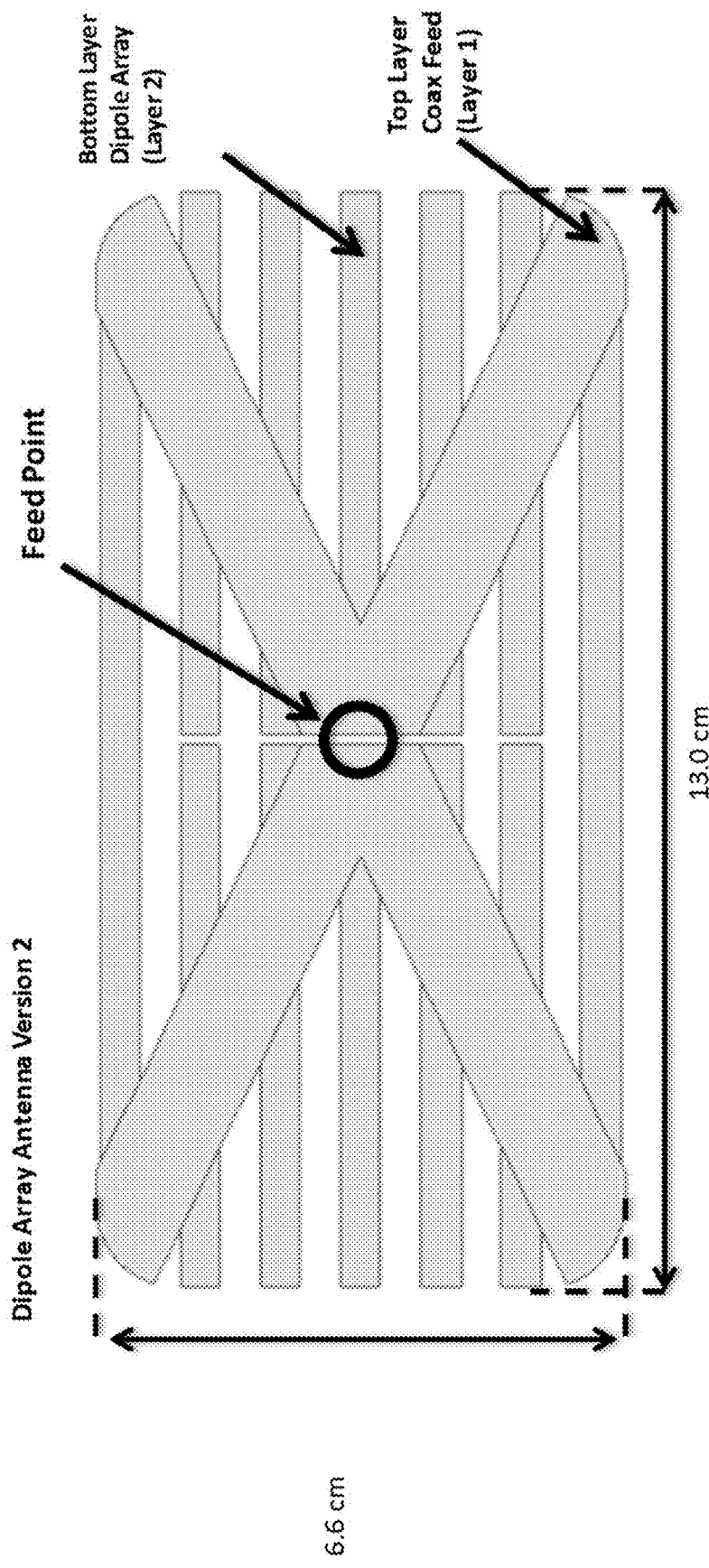
FIGS. 14A to 14G show additional examples of antenna designs.
Figure 14B:
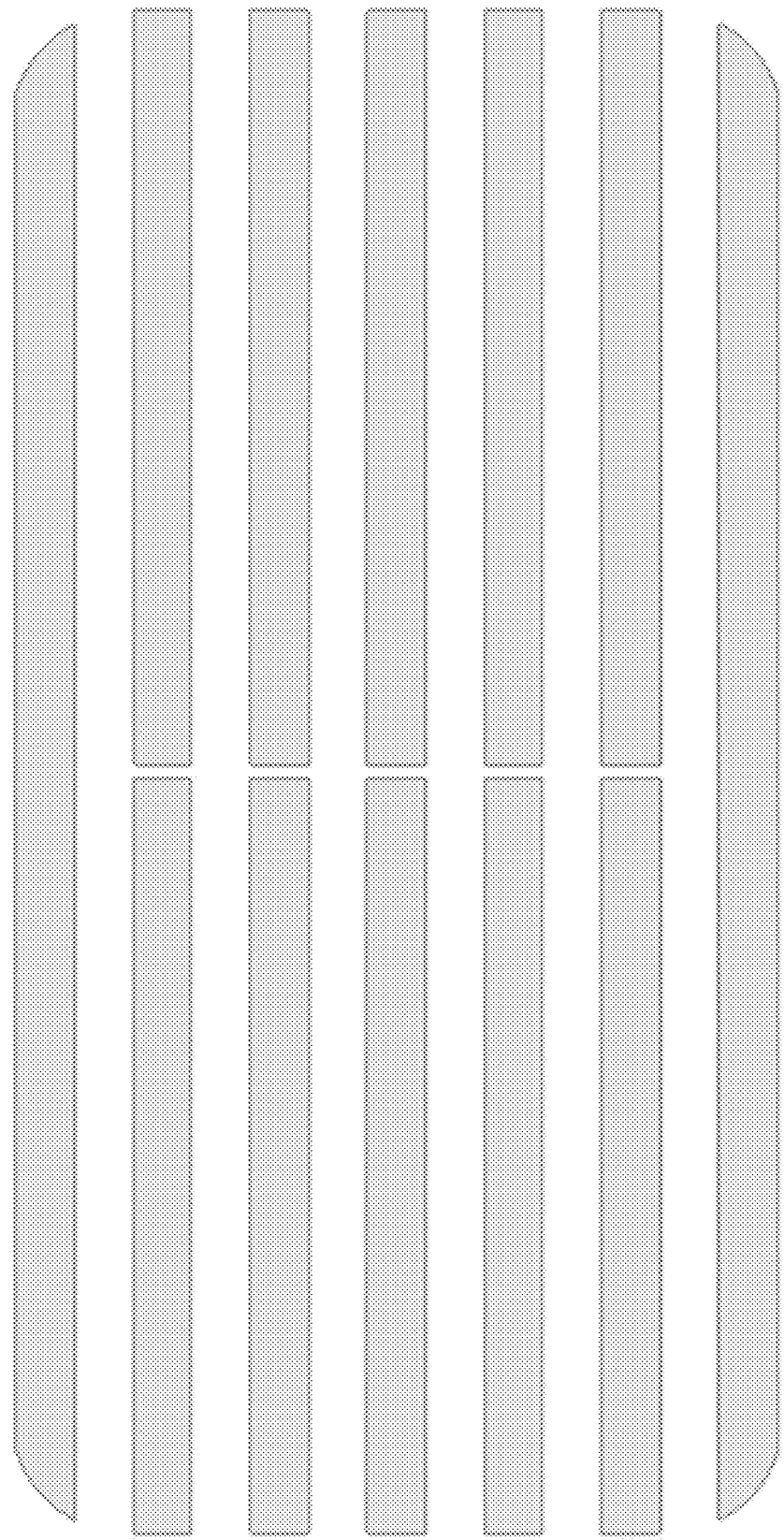
Figure 14C:
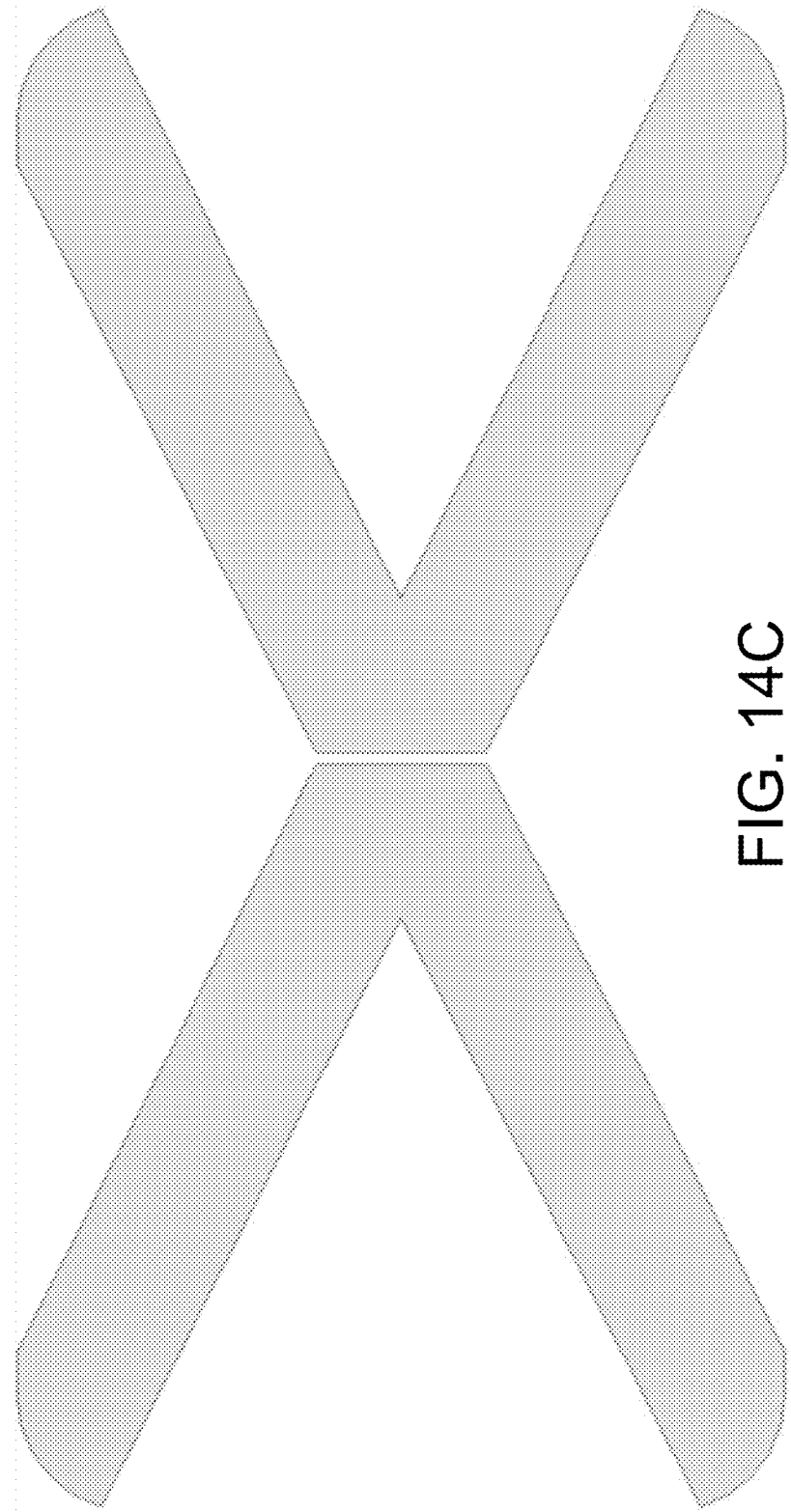

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
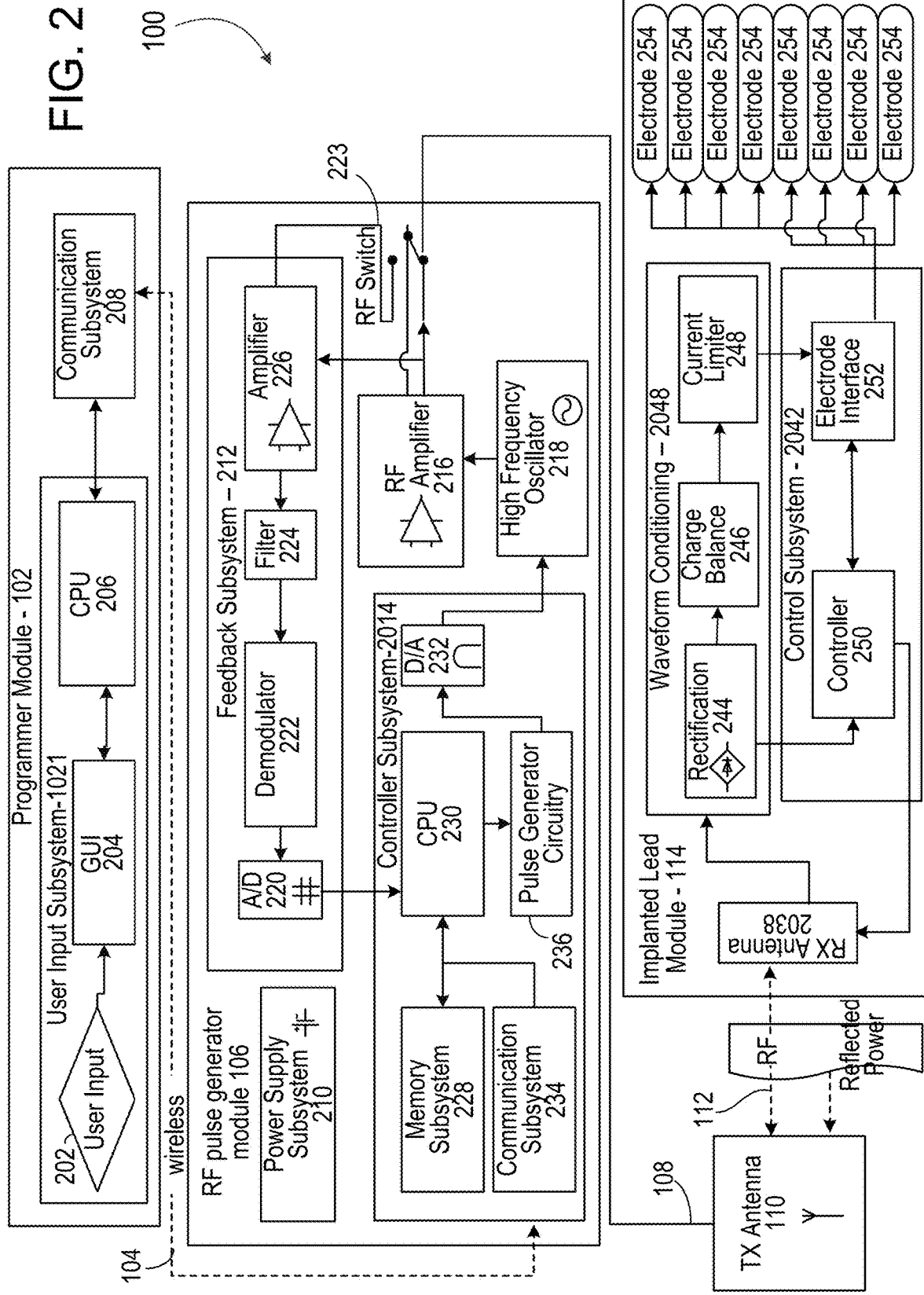
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
| --- | --- |
| Pulse Amplitude: | 0 to 20 mA |
| Pulse Frequency: | 0 to 10000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm². In order to avoid the irreversible electrochemical reactions such as pH change, electrode dissolution as well as tissue destruction, no net charge should appear at the electrode-electrolyte interface, and it is generally acceptable to have a charge density less than 30 uC/cm². Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

In some applications, the transmit antenna 110 can be placed in close proximity to the receiving antenna 238. For example, the transmit antenna 110 may be worn by the patient. In other examples, the transmit antenna 110 may be placed further away from the patient (and the implanted passive neural stimulator that houses receiving antenna 238). In the former case, less energy may be emitted from the remote antenna to wirelessly provide power and stimulation parameter settings to the passive neural stimulator. In some scenarios, the patient may remain stationary or asleep. During sleep, the patient may not desire to wear a transmitting antenna 110 that is coupled to a controller module (such as controller subsystem 214) through a cable. An antenna assembly may be used to remotely provide power and stimulation parameter settings to the passive neural stimulator. The antenna assembly in this example may be more than 10 centimeters away from the passive neural stimulator implanted inside a patient. If the patient can move around a room; the entire room may need to be illuminated with the microwave energy field. In this scenario, an array of antennas, or a broad beam-width antenna, may be used. Some implementations may incorporate a steerable (e.g., mechanically, electrically) arrangement of antennas that include a receiving antenna location tracking system. These implementations may further apply motion control of the transmitting antenna 110 to adjust angle or orientation of illumination of an antenna to point in the direction of the receiving antenna. The output power is adjusted as needed depending on the distance between the transmitting and receiving antennas and the directivity of the transmitting antenna.

Recent years have seen a surge of demand for wearable antennas that are flexible in shape to tailor to that of human body and robust to withstand daily wear and tear. Indeed, wearable antennas can be used for radiating from the body surface into air, and receiving a signal from air on the body surface. While some examples may use wearable antennas primarily for RF communications, some implementations disclosed herein employ wearable antenna to radiate RF energy into the body to wireless power and communicate with a passive stimulator device implanted in the patient.

Patient ergonomics and comfort mandate the wearable antennas to be thin, light weight, flexible, and conformal to the body. These traits need to be reconciled with performance characteristics for the substrate materials to be lossless and electrically stable when introduced to the body. Specifically, the materials need to be breathable but must not absorb or retain moisture, which may cause changes in antenna electrical properties, and therefore the antenna performance. In addition, the flexible ground and signal layers need to be of highly conductive material.

Two general types of antennas may be used for transmitting RF energy into the body, namely, the patch antenna and the dipole antenna. The patch antenna contains a ground plane and a signal plane that are separated by a dielectric substrate. The dipole antenna contains two arms, the signal and ground, which typically lie in the same plane.

In the case of the patch, the substrate material that separates the metal layers largely influences the design and performance of the antenna. For example the substrate dielectric value influences the size of the patch antenna needed to resonate at a particular frequency. The aperture size, the size of the radiating metal layer of the antenna, determines the focus (or spread) of energy transmitted into the body. Thus the dielectric value must be chosen carefully to simultaneously radiate at the desired frequency and focus the energy into the body. Also, the thickness of the dielectric layer influences the radiating bandwidth of the antenna. Typically, the bandwidth increases with thickness of the dielectric layer.

The following are examples of antenna designs that can be made from conductive fabric: a flexible patch antenna, flexible dipole antennas, and variations of flexible dipole array antennas. Antennas may be sized for 915 MHz, but inventive concept is not limited to any frequency range. For illustration in this document, images are to scale for 915 MHz, unless otherwise noted.

Figure 3A:
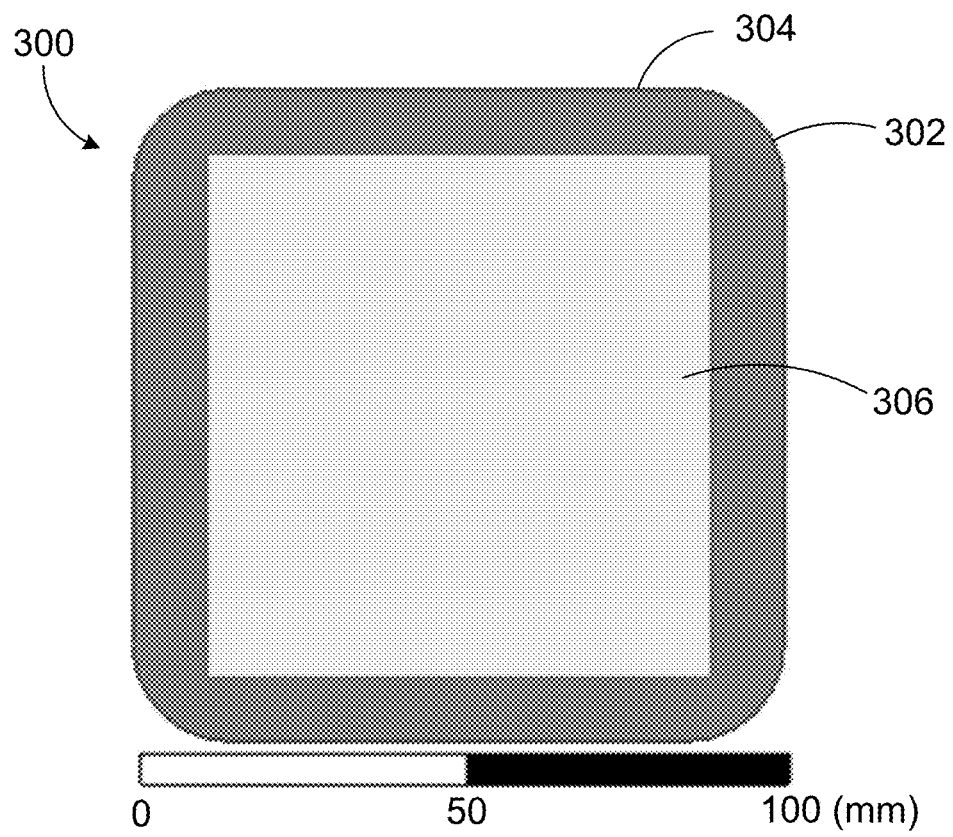
FIG. 3A shows a top view of an example of a patch antenna.

FIG. 3A shows a top view of an example of a patch antenna 300. As illustrated, the top surface 302 includes rim area 304 and center area 306. In some instances, the example of patch antenna design can be attained with the use of existing microwave circuit board laminate material, however, the laminate board antenna lacks the desired flexibility.

In some cases, low loss, high dielectric, flexible substrate may be used for a patch antenna that include, for example, high dielectric ceramic fabric, flexible elastomeric dielectric flexible silicone rubber sheet with dielectric constants ranging from, for example, 2 to 30, or silicone rubber base that is mixed with titanium dioxide. In some implementations, however, conductive fabric material.

Figure 3B:
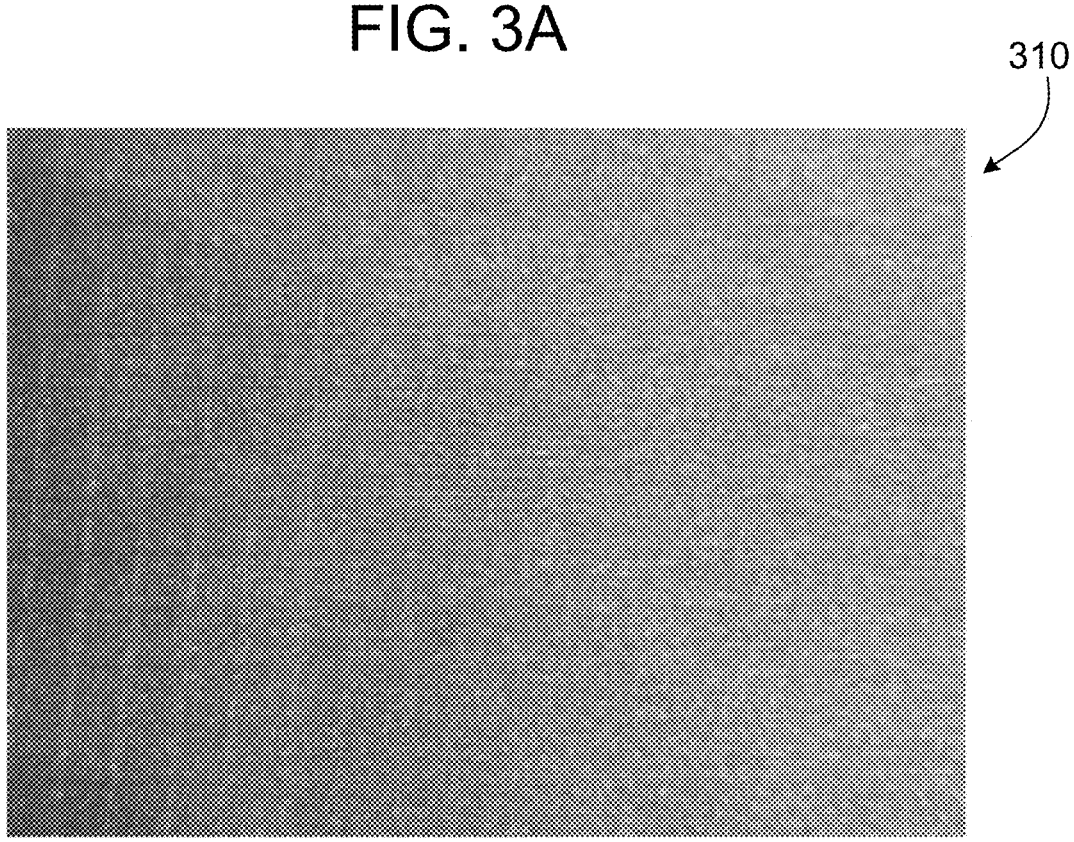
FIG. 3B shows a top view of an example of conductive fabric material as a layered structure.

FIG. 3B shows a top view of an example of conductive fabric material 310 as a layered structure. In general, fabrics that are comfortable to the skin are made of materials such as cotton, which have a low dielectric constant and propensity to absorb moisture, which causes variability in the material's effective dielectric constant. When using cotton or other dielectrics close to that of air, the example of patch may include a substrate size that is impractically large. In some instances, the antenna can be oversized for ergonomics and comfort, spreading the transmitted field pattern to hinder effective distribution of power wirelessly to the implanted device. The primary component of a flexible antenna is a flexible conductive material to be used for the antenna signal and ground metals. It is desirable for the material to be breathable, however, conductivity of the material may be maintained for antenna performance.

Figure 3C:
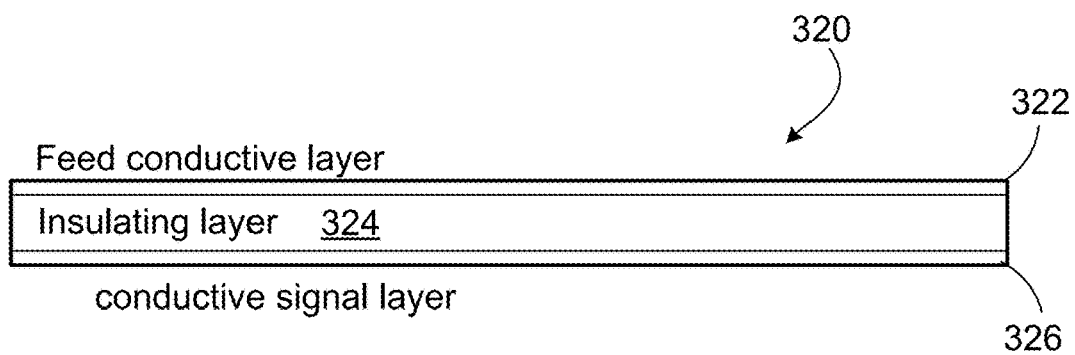
FIG. 3C shows a cross-sectional view of an example of a layered antenna.

In one example, the conductor may be made of material from metal fabric sheets such as conductive metallized nylon fabric. In another example, the conductor may be made of copper-clad flexible laminated composites. In other examples, fabric antennas may be made by embroidering of conductive thread of antenna into a fabric, or printing of a conductive ink onto a fabric to from the antenna conductive fabric shape. FIG. 3C shows a cross-sectional view of an example of a layered antenna 320 with a feed conductive layer 322, insulating layer 324, and conductive signal layer 326. While the y conductive signal layer 326 may function as a radiating surface to non-inductively couple energy wirelessly into an implantable stimulator device implanted underneath the skin, the feed conductive layer 322 may be on the opposite side of the insulating layer and away from the skin. The feed conductive layer 322 capacitively couples to the conductive signal layer 326. In some implementations, the feed conductive layer 322 may be represented by the X-shaped metal layout, as will be discussed in more detail below.

Figure 4A:
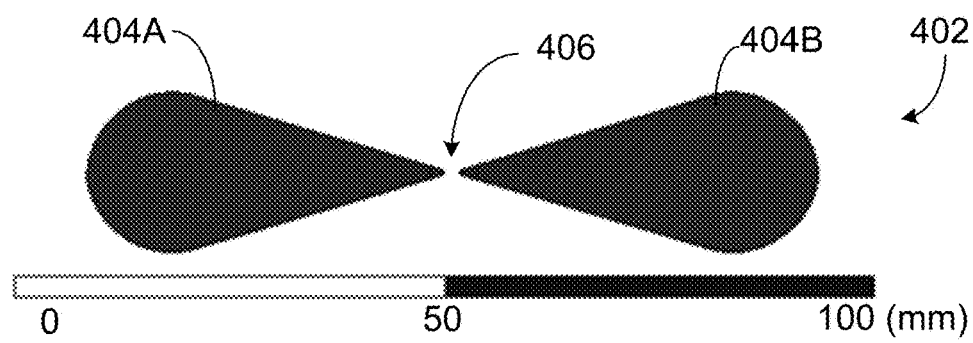
FIGS. 4A to 4E show the various shapes of examples of dipole antennas.

FIGS. 4A to 4E show the various shapes of examples of dipole antennas. FIG. 4A shows an example of a bowie-shaped antenna 402 with arms 404A and 404B, as well as a feed port 406. One arm is connected to the signal conductor and the other is connected to the ground. In order to connect the RF supply coax at the feed port 406 of the antenna, it may be advantageous for the feed port to have a small cooper pad, to distribute the connection to the feed cable inner and outer conductors over a small area of the conductive fabric. This can strengthen the mechanical connection and enhance the electrical connection.

Figure 4B:
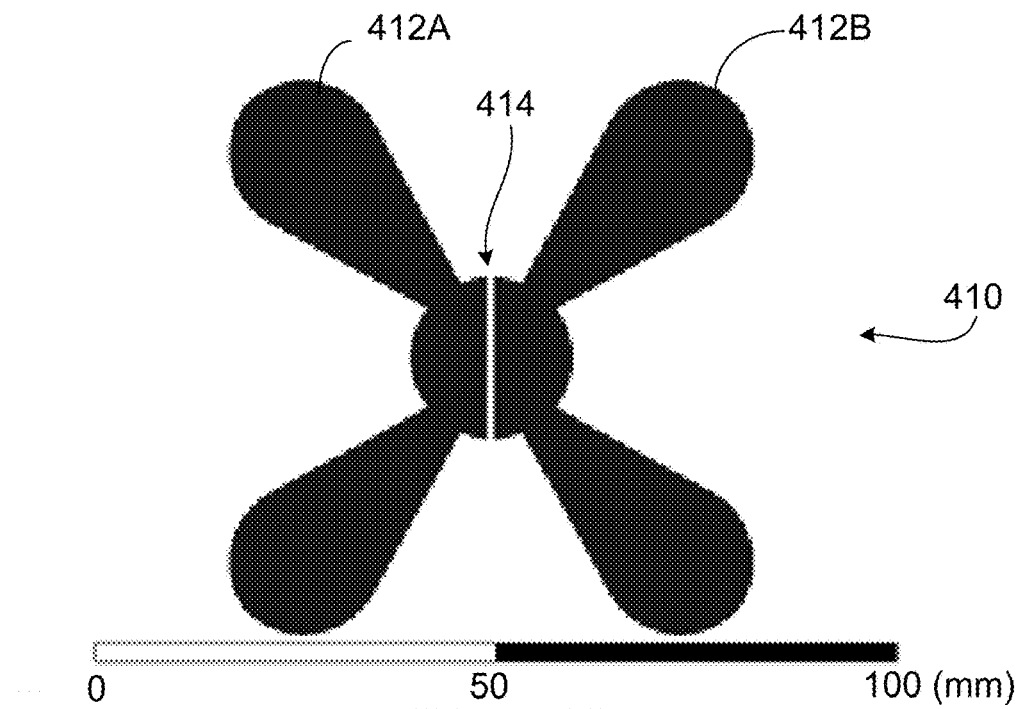
Figure 4C:
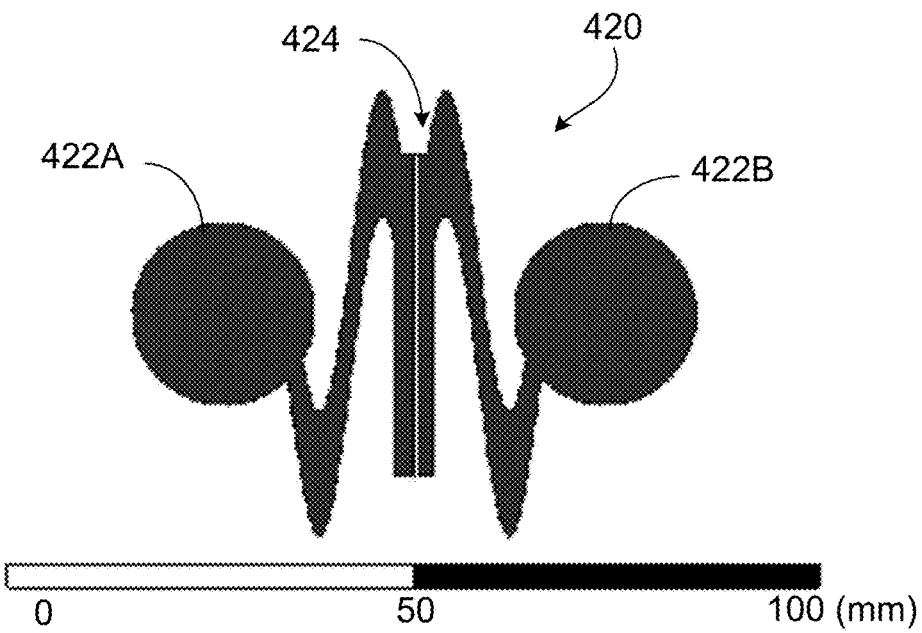

FIG. 4B shows an example of an antenna 410 in the shape of a double bowtie. Antenna 410 has two arms, namely 412A and 412B, each having two leaves. The two arms 412A and 412B converge on feed port 414. One arm is connected to the signal conductor and the other is connected to the ground. FIG. 4C shows another example of an antenna 420 with two arms. Antenna 410 has two arms, namely 422A and 422B that are symmetric in shape. Each arm includes a circular surface electrically connected, through a conducting surface in random, but not erratic, shape, to feed port 424.

Figure 4D:
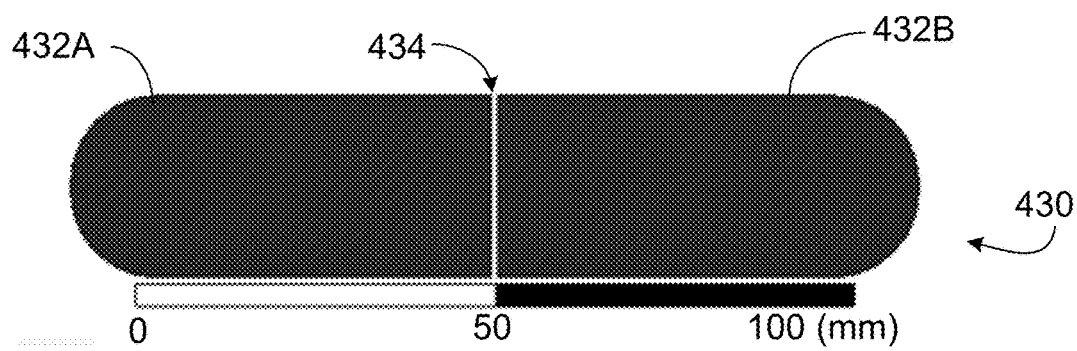
Figure 4E:
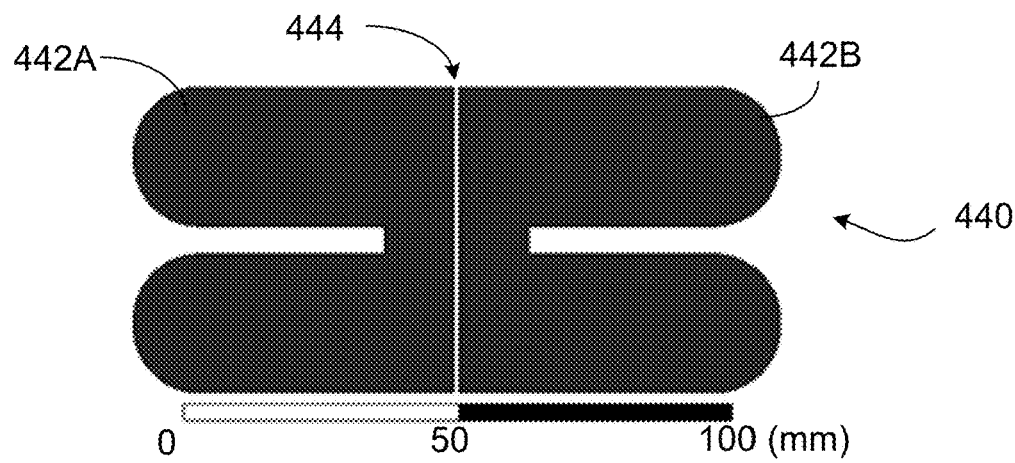

One arm is connected to the signal conductor and the other is connected to the ground. FIG. 4D shows yet another example of an antenna 430 in a bandaid-shape with two arms connected to feed port 434. One arm is connected to the signal conductor and the other is connected to the ground. FIG. 4E shows still another example of an array 440 having two arms, namely 442A and 444B. Each arm has two band aid halves that are conductively connected. The two arms 442A and 444B connect at feed port 444.

Figure 4F:
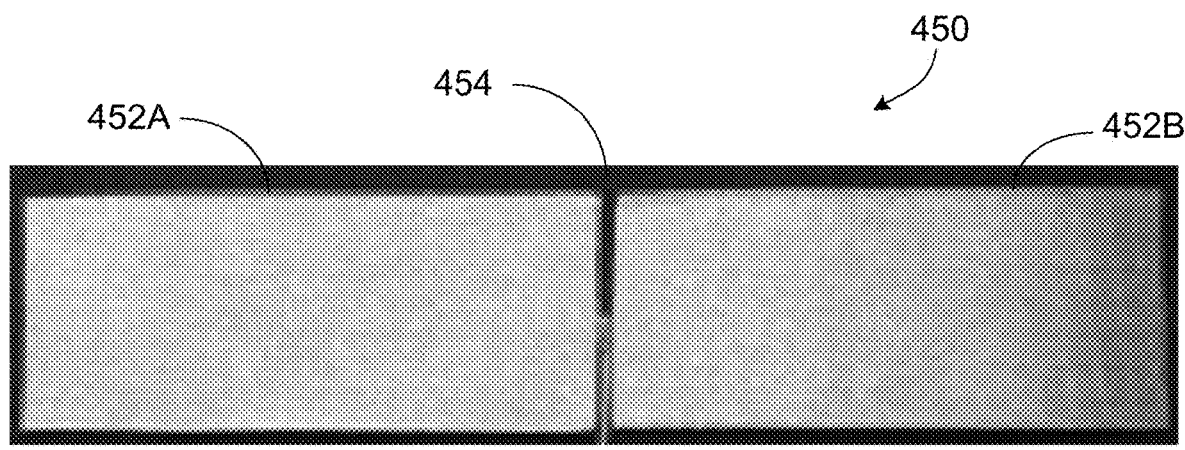
FIG. 4F shows a top view of an example of a dipole antenna made from conductive fabric.

These dipole antennas can be made using the conducting fabric as shown in FIG. 3B. FIG. 4F shows a top view of an example of a dipole antenna prototype 450 made from conductive fabric. The two arms 452A and 452B are made from conductive fabric and are connected at feed port 454, which can connect to a RF connector, such as, for example, a BNC or SMA connector.

Figure 5A:
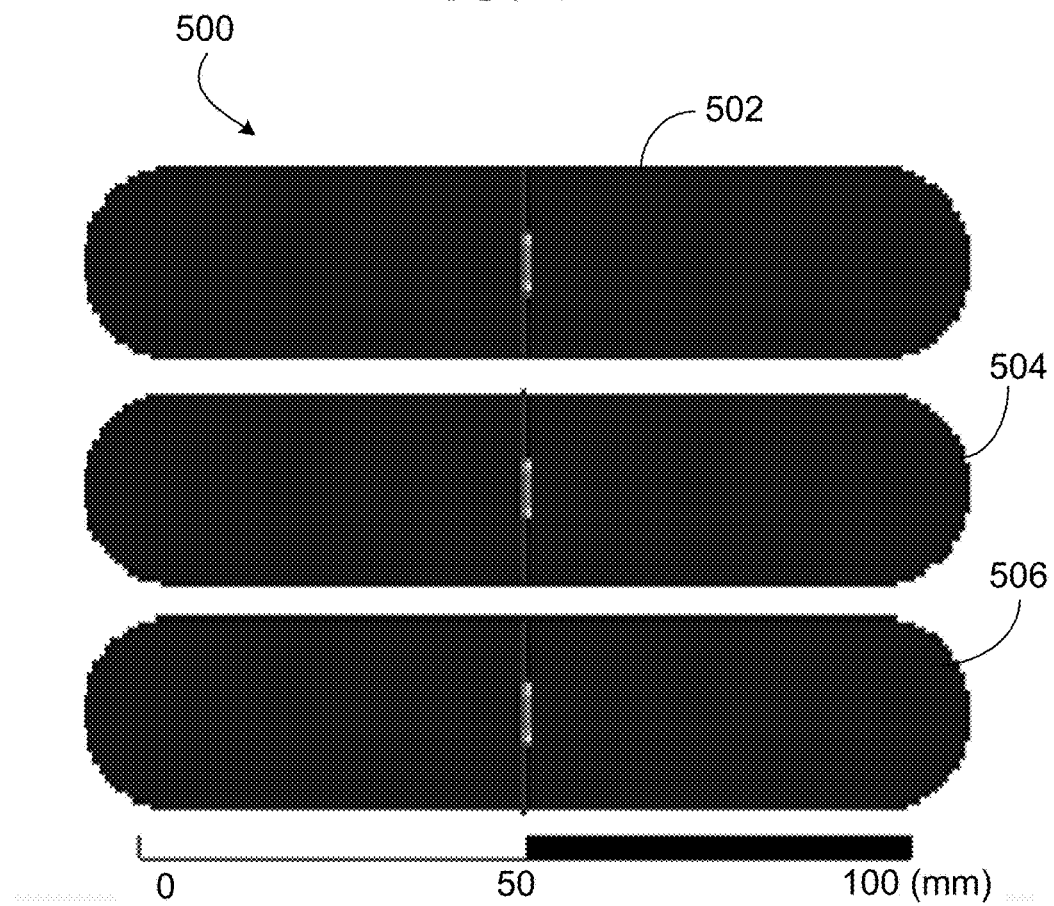
Figure 5B:
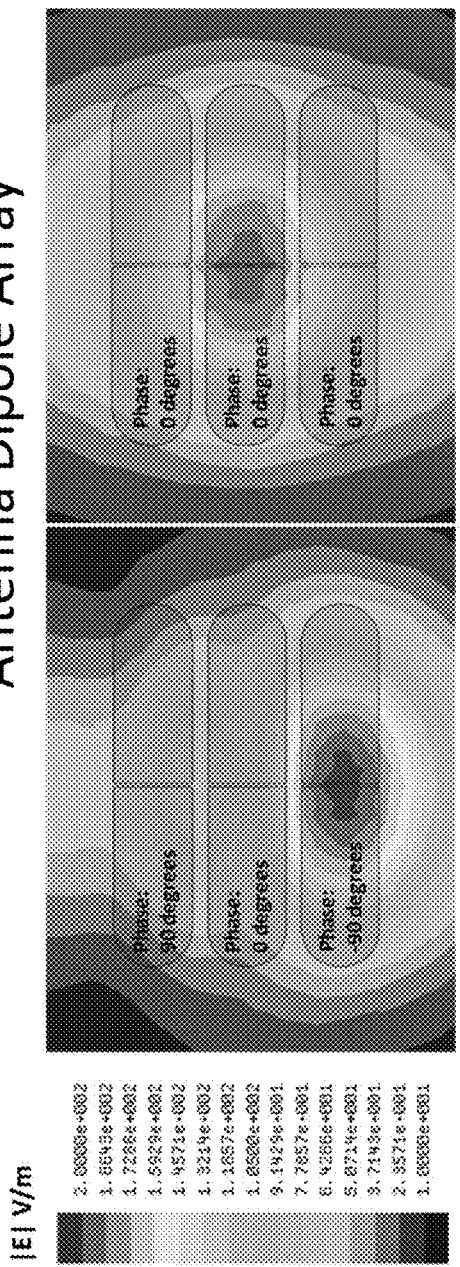
FIG. 5B shows its phase-controlled electric field distribution pattern at 5 cm depth.
Figure 5B:
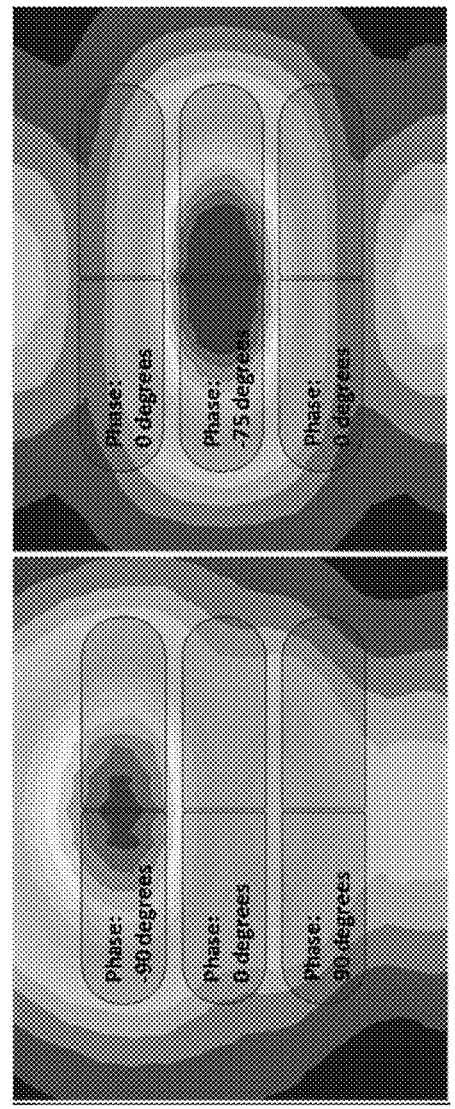

Based on the dipole antenna, an array of dipole antennas can be made. FIG. 5A shows an example of shapes of an array 500 of dipole antennas having three band aid-shaped dipole antennas 502, 504, and 506. There are at least two significant advantages to using an array of antennas compared to using a single antenna. One such advantage is the ability to distribute power as it enters the body, thereby reducing SAR hot spots at the patient's skin. The other advantage is the ability to focus the transmitted energy in the body, for more efficient energy transmission. By way of an illustrative example, the phase (or delay time of the pulse) of the individual antennas of FIG. 5A can be controlled so that the radiated electric field from the antenna array interferes constructively in front of the antennas. FIG. 5B shows the simulated electric field results due to constrictive interference at a plane 5 cm deep of a HFSS human average phantom (as discussed in an example in FIG. 8).

FIG. 5B demonstrates the importance of the connections to each of the antennas and the timing of signal arrival at the individual antenna feed ports. In particular, each band aid bar has its own feed port that can be driven If the phase is incorrect, constructive interference may not occur at the intended area to realize the gains that would have resulted from the use of multiple transmitting sources. The electric field from all of the antennas can be superposed at the same spot at the same time (focused) such that maximum field intensity can be attained and energy is not wasted. Energy can be wasted when the field levels are not high enough to activate the stimulator. All of the light grayness area in FIG. 5B represents energy that is unduly spread out (unfocused) and therefore can be wasted without reaching a sufficient intensity to activate the passive implantable stimulator device. The lower right image in FIG. 5B can represent an improvement with the array of three band aid antennas. This example shows that by driving the central band aid bar with a voltage input that has a phase delay of 75 degree (as shown in the lower right of FIG. 5B) compared to the upper and lower band aid bars from FIG. 5A, a more pronounced of E-field distribution may be generated, as compared to driving all three band aid bars with no phase variation (as shown in the upper left of FIG. 5B). In this example of FIG. 5B, each band aid bar is individually driven by a voltage input. Connecting a single feed cable to multiple antennas via splitters may not be practical when more than a few antenna elements are used. Some implementations may use a second layer of metal separately connecting to each of the multiple connector feeds.

Figure 6A:
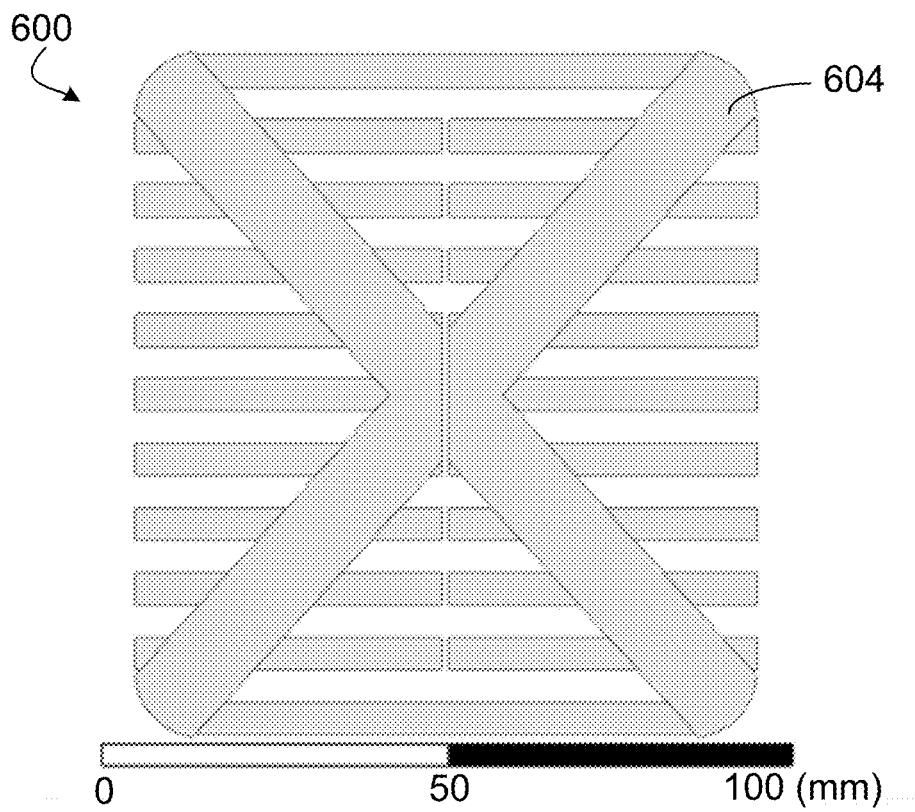
FIGS. 6A to 6C show examples of dipole antenna arrays with collective feed implemented as a second layer of connecting metal.
Figure 6B:
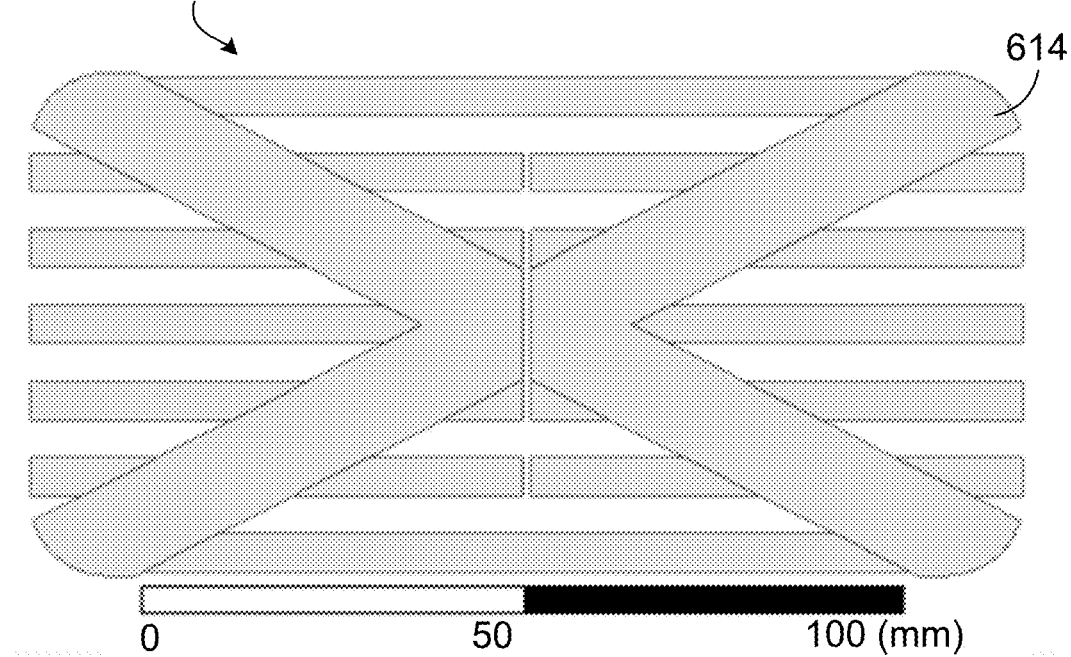
Figure 6C:
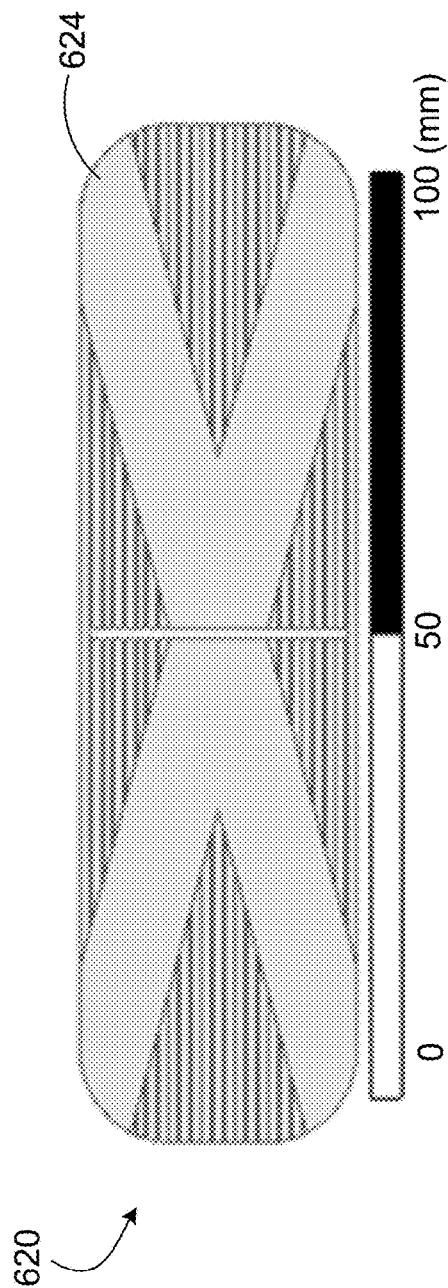

In more detail, FIGS. 6A to 6C show examples of respective dipole antenna arrays 600, 610, and 620 with collective feed implemented as a second layer of connecting metal. The feed conductive layer is represented by the respective x-shaped metal layout 604, 614, and 624 exposed in the dipole array antenna figures. The capacitive connection to the individual antennas are located at various positions along the length of the antennas. This distributed connection to the antennas enables a distributed phase configuration for the antennas in the array. An example of the resulting focusing of energy is shown in FIG. 12C, where the field of the dipole array antenna (bottom) is compared to that of a patch antenna (top). In the examples of FIGS. 6A to 6C, the RF connection to the antennas in the array of the conductive layer is an alternating current connection through in insulating layer, which will be of fabric, as described in FIGS. 3B to 3C.

Figure 7:
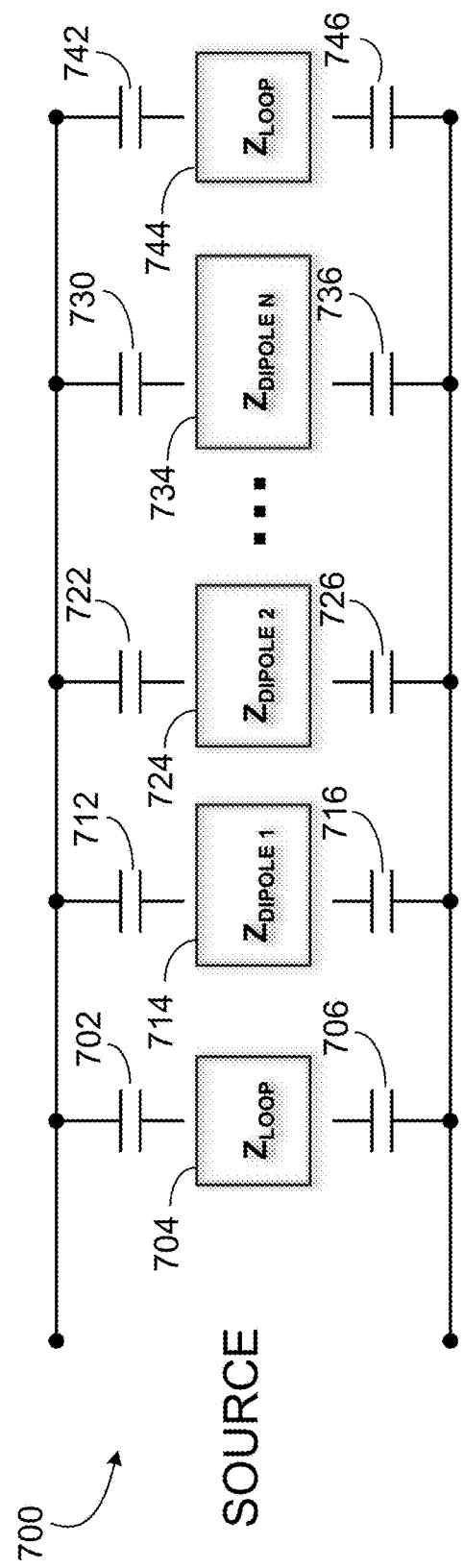
FIG. 7 shows a diagram of an example of a simplified equivalent circuit model for a dipole antenna array.

FIG. 7 shows a diagram of an example of an equivalent circuit model 700 for a dipole antenna array. Model 700 includes a capacitive network in which several branches are connected in parallel. Each of the branch includes a first capacitive load, an impedance load, and a second capacitive load in serial connection. For example, load 702, load 704, and load 705 are serially connected on a first branch. Similarly, load 712, load 714, and load 716 are serially connected; load 722, load 724, and load 726 are serially connected; load 732, load 734, and load 736 are serially connected; load 742, load 744, and load 746 are serially connected.

Figure 8:
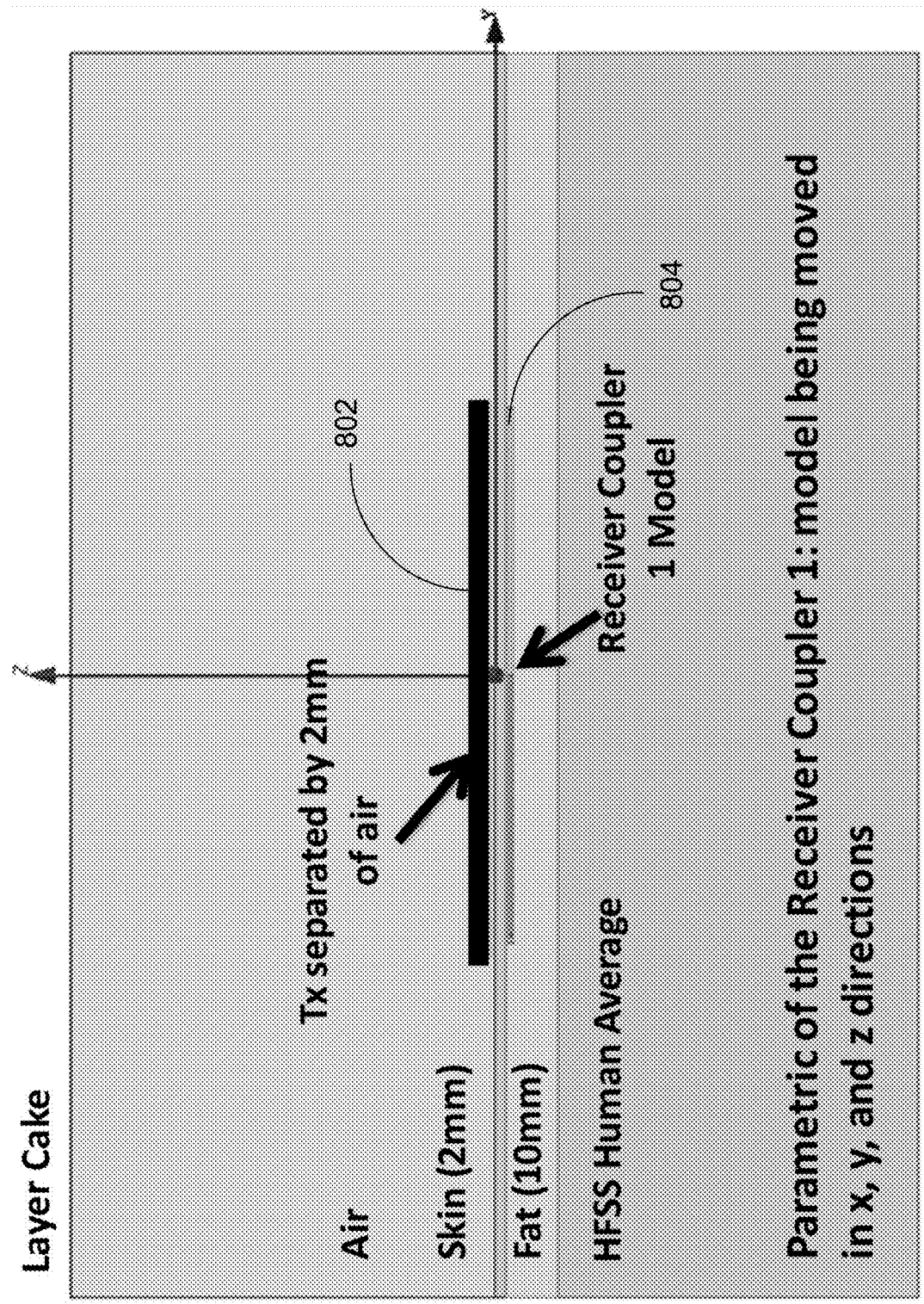
FIG. 8 shows an example of a scenario for simulating transmission and reflection performances of dipole antenna arrays.

FIG. 8 shows an example of a scenario 800 for simulating transmission and reflection performances of dipole antenna arrays. Here, radiating surface 802 is placed 2 mm above the skin that has 10 mm-thick fat layer underneath. The implantable stimulator device 804 may be placed at various depths under the skin, for example, in the fat layer.

Figure 9:
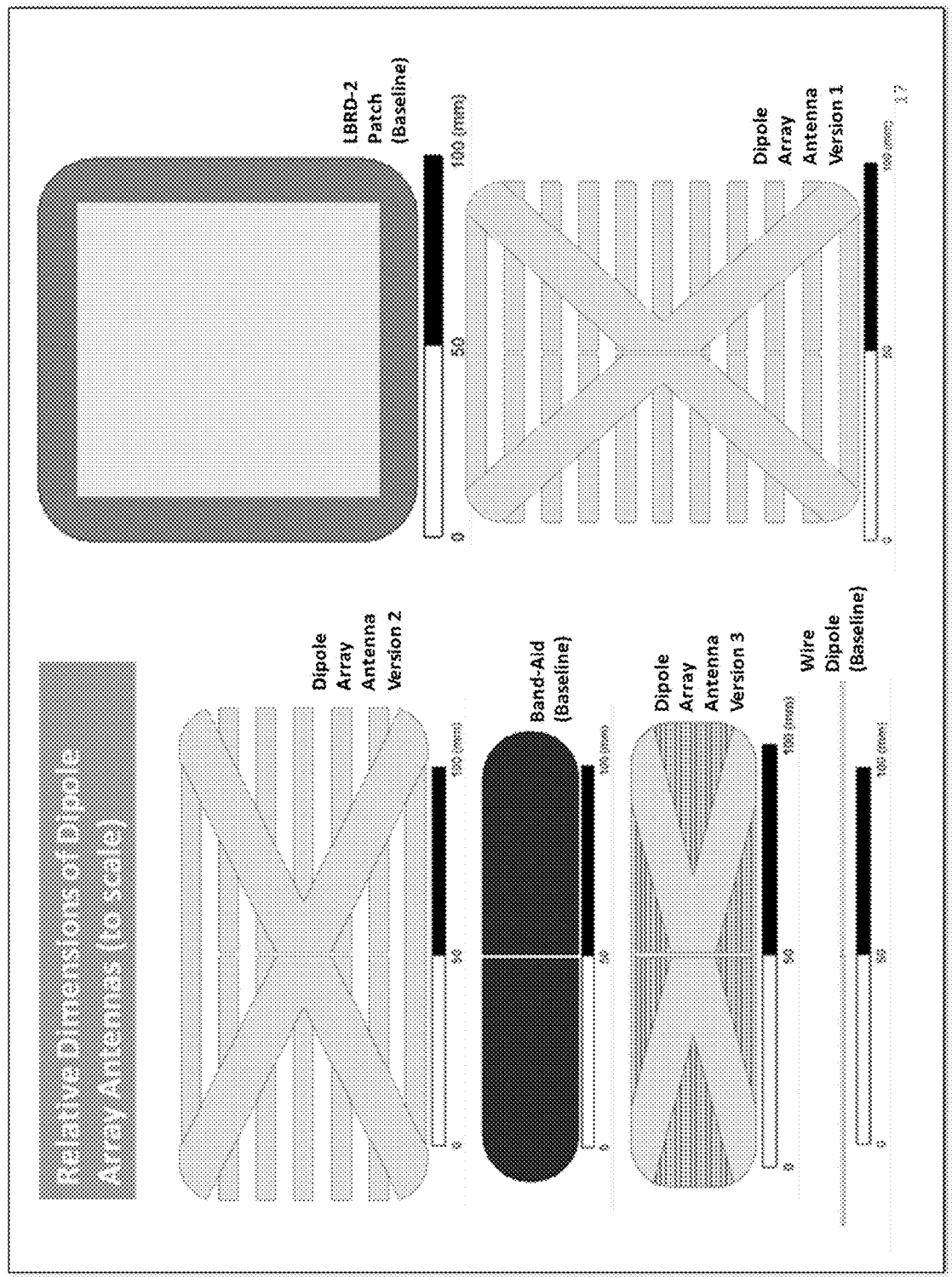
FIG. 9 shows examples of antenna designs.

Referring to FIGS. 9 to 14, examples of antenna designs are demonstrated with corresponding characteristics. FIG. 9 shows the arrangements of three versions of dipole array antenna, namely, dipole array antenna version 1, dipole array antenna version 2, dipole array antenna version 3. As illustrated in further detail in FIGS. 14A to 14G, each dipole array has two conductor layers, namely a top conductor layer with coax feed (layer 1) and a bottom conductor layer (layer 2). In the configurations, for example, shown as versions 1 to 3, the top layer includes a cross in the shape of an "X." The cross has a left half and a right half, as illustrated. A feed point is located at the confluence region between the two halves. The feed point may include an interface to, for example, a coax cable. An example of a coax cable is shown in FIG. 14G. The coax cable may, in turn, connect to a portable Microwave Field Stimulator (MFS) device, such as the one illustrated in FIG. 2. The bottom conductor layer includes several bar-shaped strips arranged in parallel. Each strip may generally have a square configuration. The two side strips (upper and lower) may include rounded edges and corners to conform to the mounting needs as the antenna device is worn by a subject. During regular daily routines, the rounded edge may provide reduces friction and laceration. FIG. 9 also shows the arrangements of three designs used as baseline configurations, namely, band aid, wire dipole, and LBRD-2 patch. The band aid configuration has an example illustrated above in, for example, FIG. 4D. The wire dipole configuration includes one wire. The patch configuration is illustrated in, for example, FIG. 3A. The size bars in FIG. 9 are presented to show scale comparison.

Figure 10A:
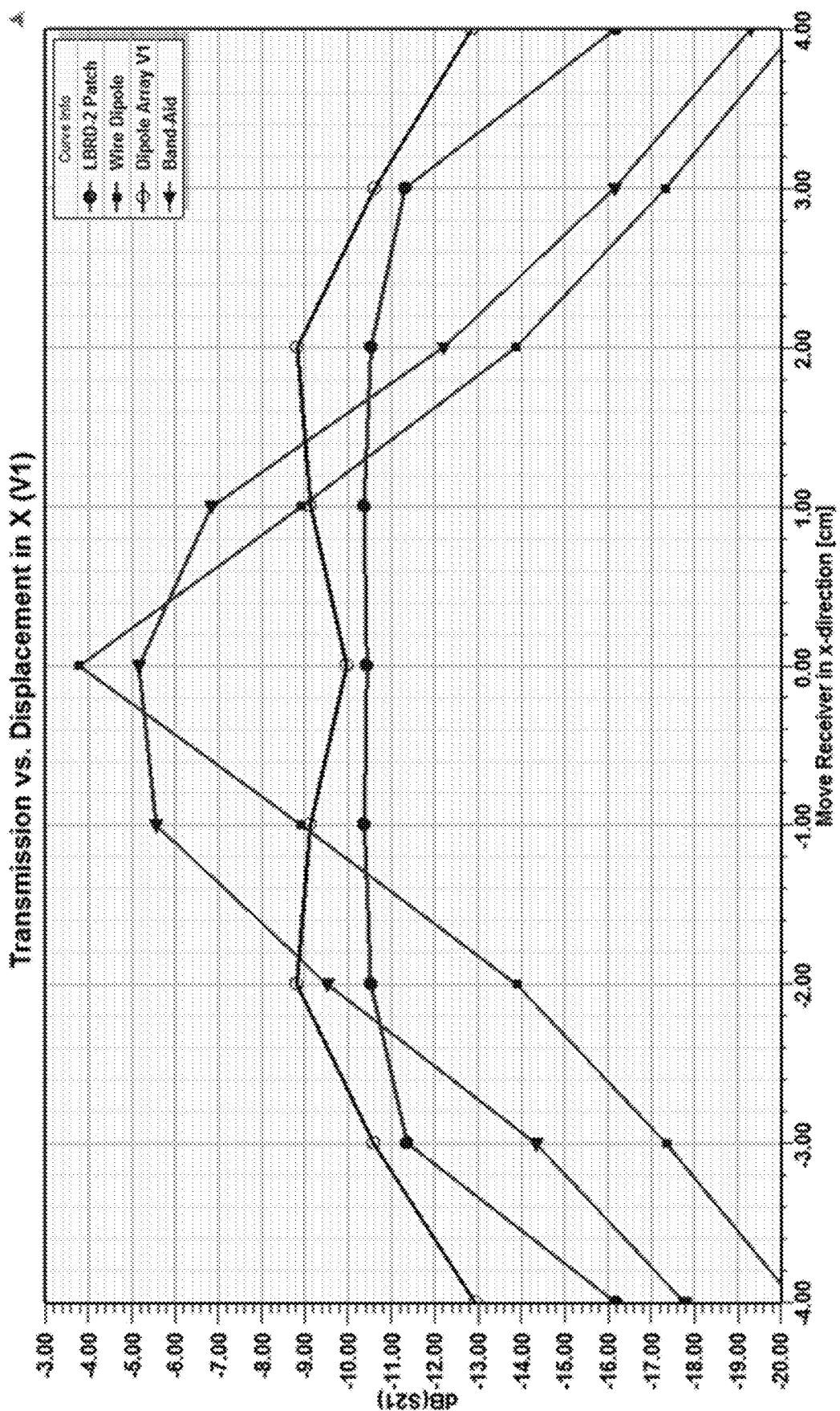
FIGS. 10A to 10C show examples of transmission profiles for of the antenna designs from FIG. 9.
Figure 10B:
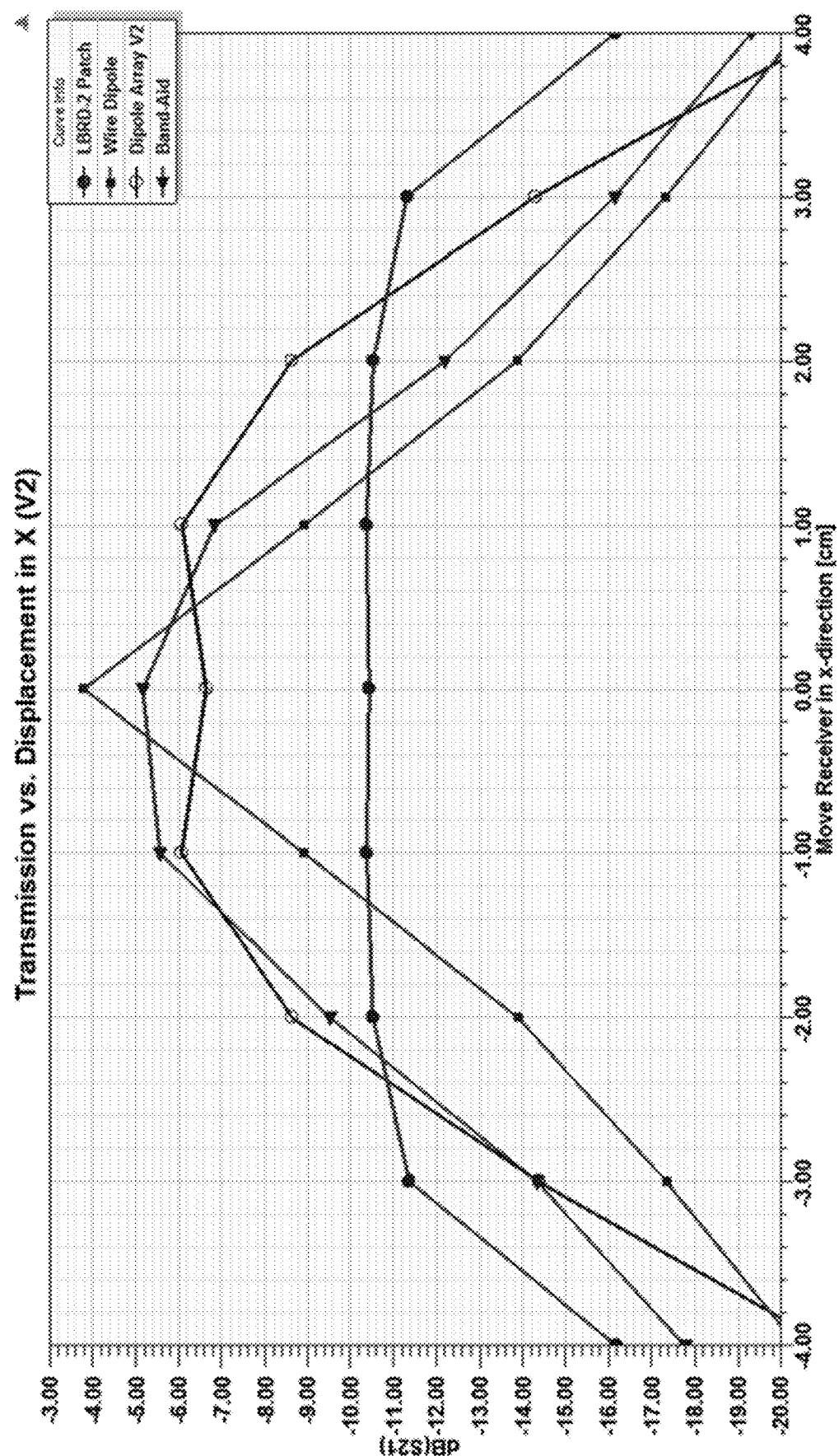
Figure 10C:
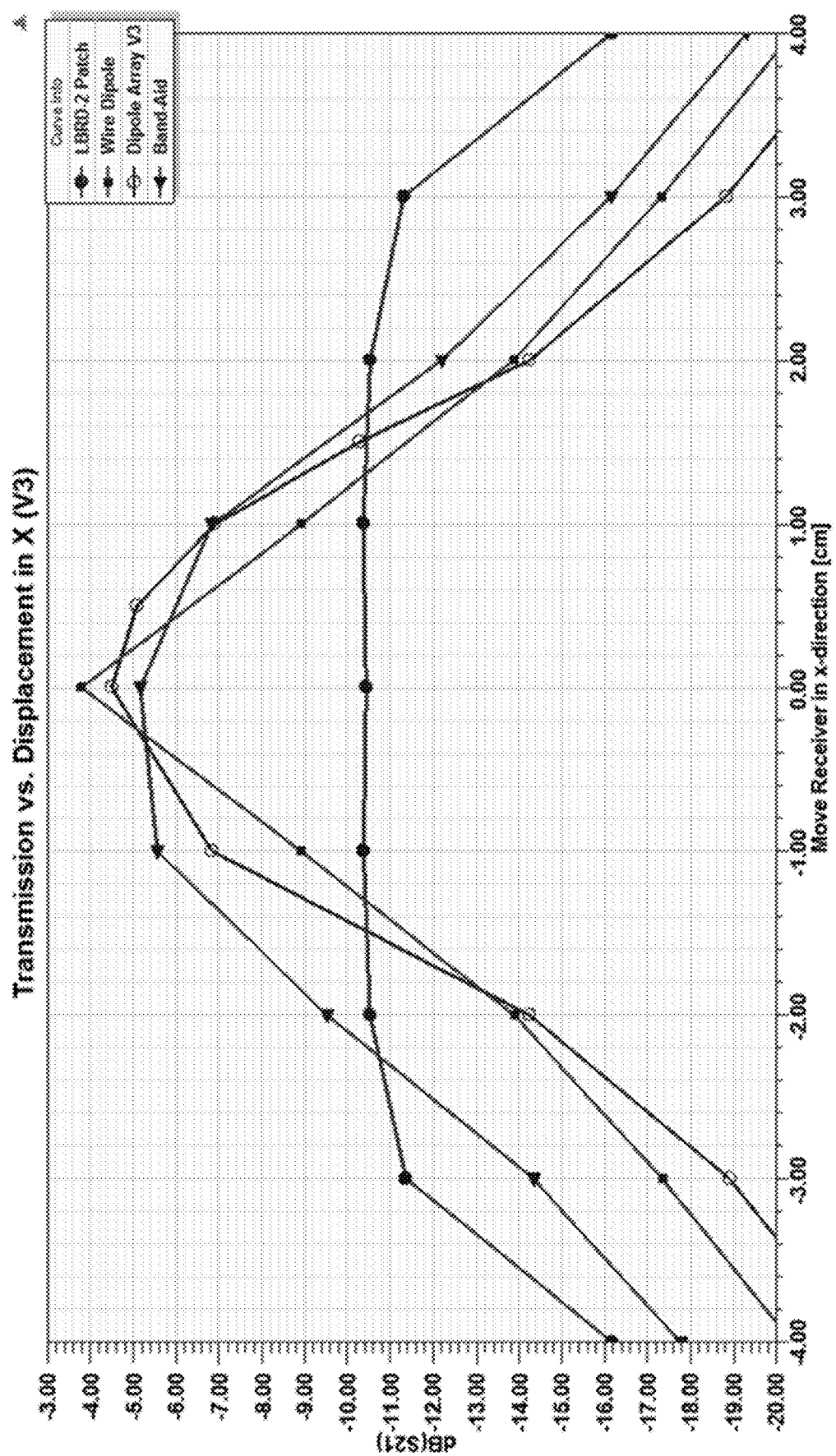

FIGS. 10A to 10C show examples of transmission profiles for a number of antenna designs from FIG. 9. As demonstrated, an array design may be optimized to achieve a more selective spatial transmission profile so that radiated energy may be more concentrated, or distributed as needed, at the location of the implantable stimulator device. Among the design configurations shown, the wire dipole configuration may exhibit the most spatially selective transmission profile while the dipole array version 1 may possess the most spatially distributed transmission profile. Such relative comparison of transmission characteristics can lead to a judicious selection of an antenna design better suited for a particular application scenario. For example, when the passive implantable stimulator device has a receiving antenna expected to span less than 1 cm in width, the transmission profile of dipole array antenna version 3 may be sufficiently uniform (e.g., fluctuates less than 2 dB over a width of 1 cm) for the purposes of supplying power to this passive implantable stimulator device.

Figure 11A:
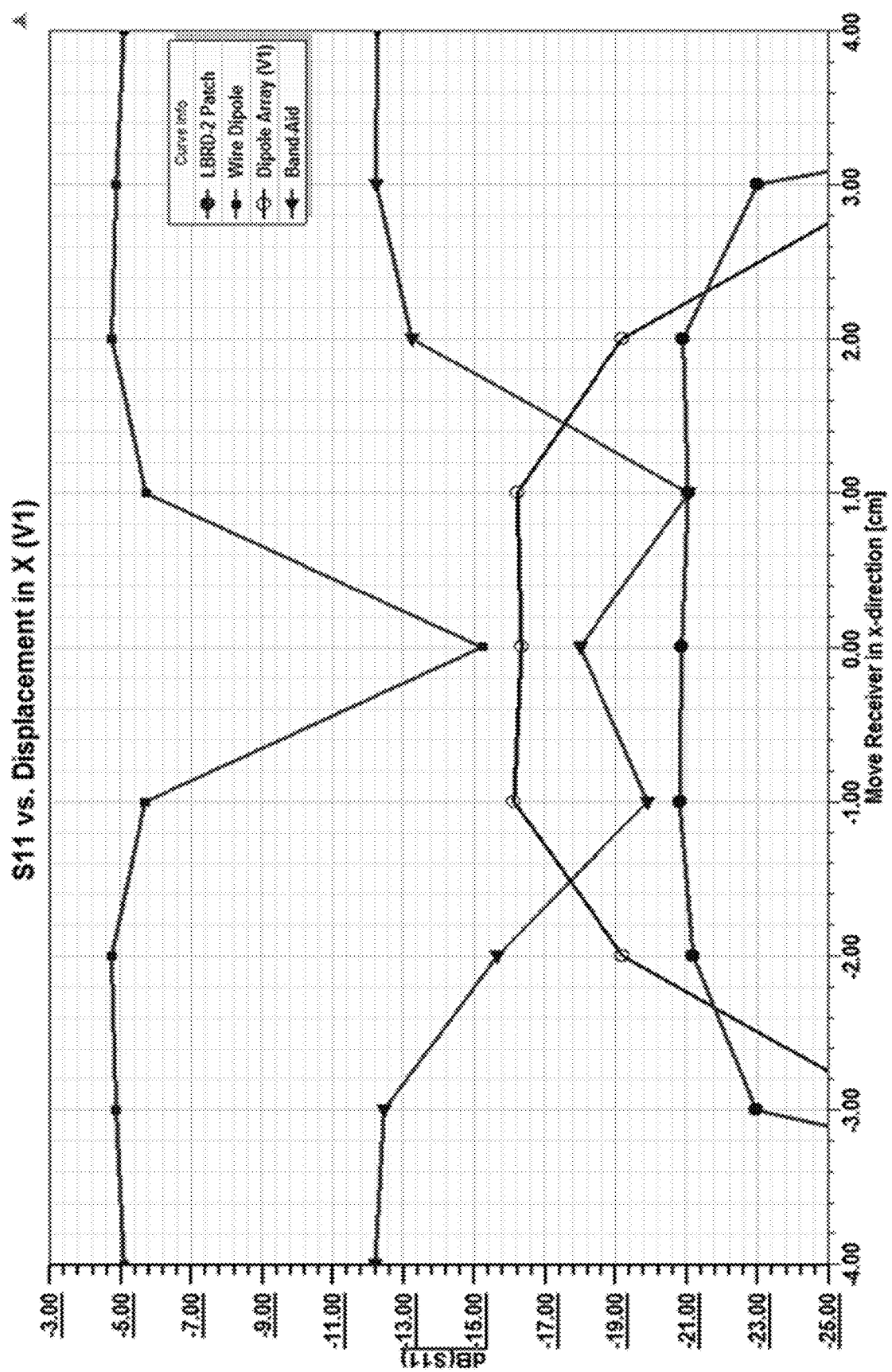
FIGS. 11A to 11C show examples of reflection profiles for the antenna designs from FIG. 9.
Figure 11B:
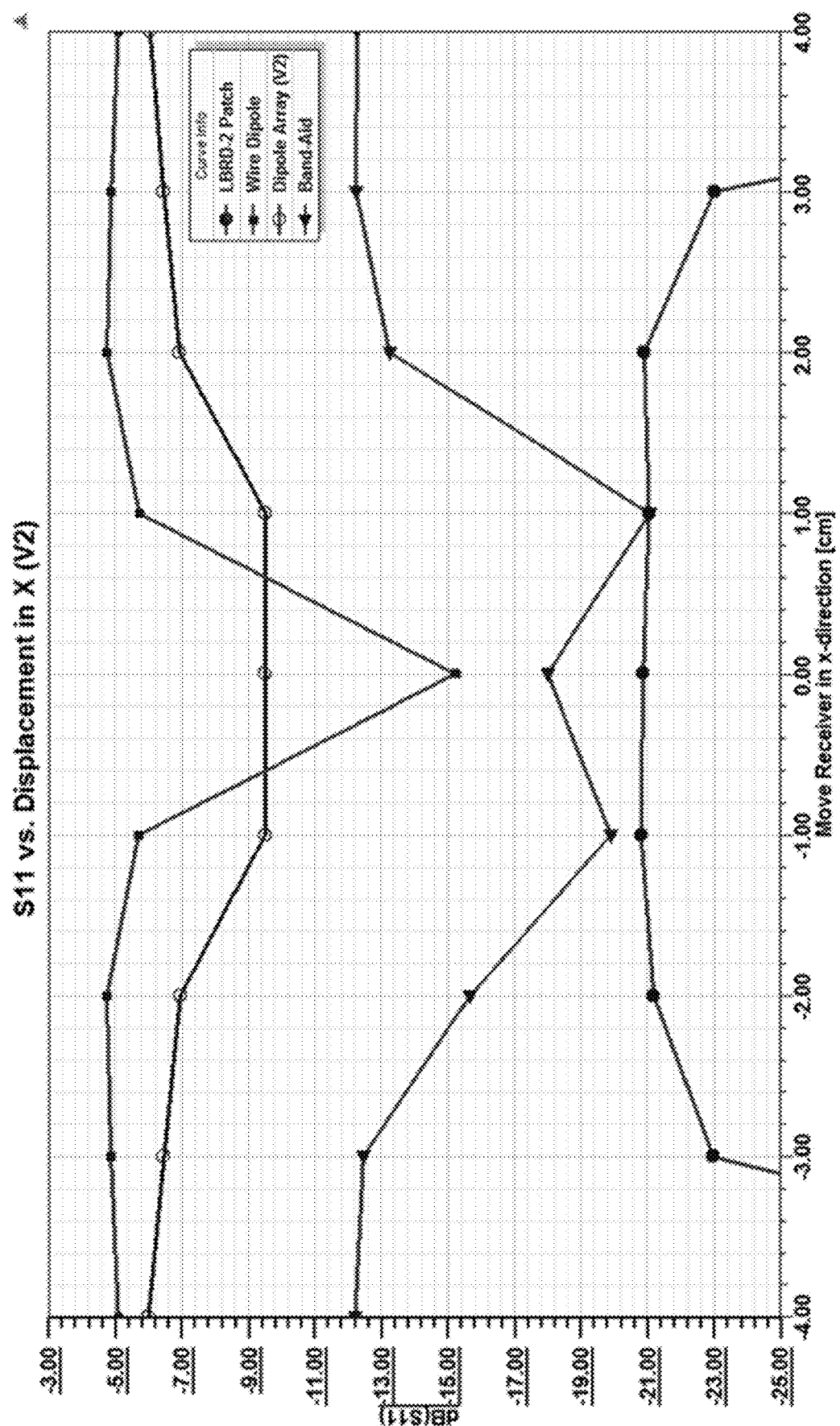
Figure 11C:
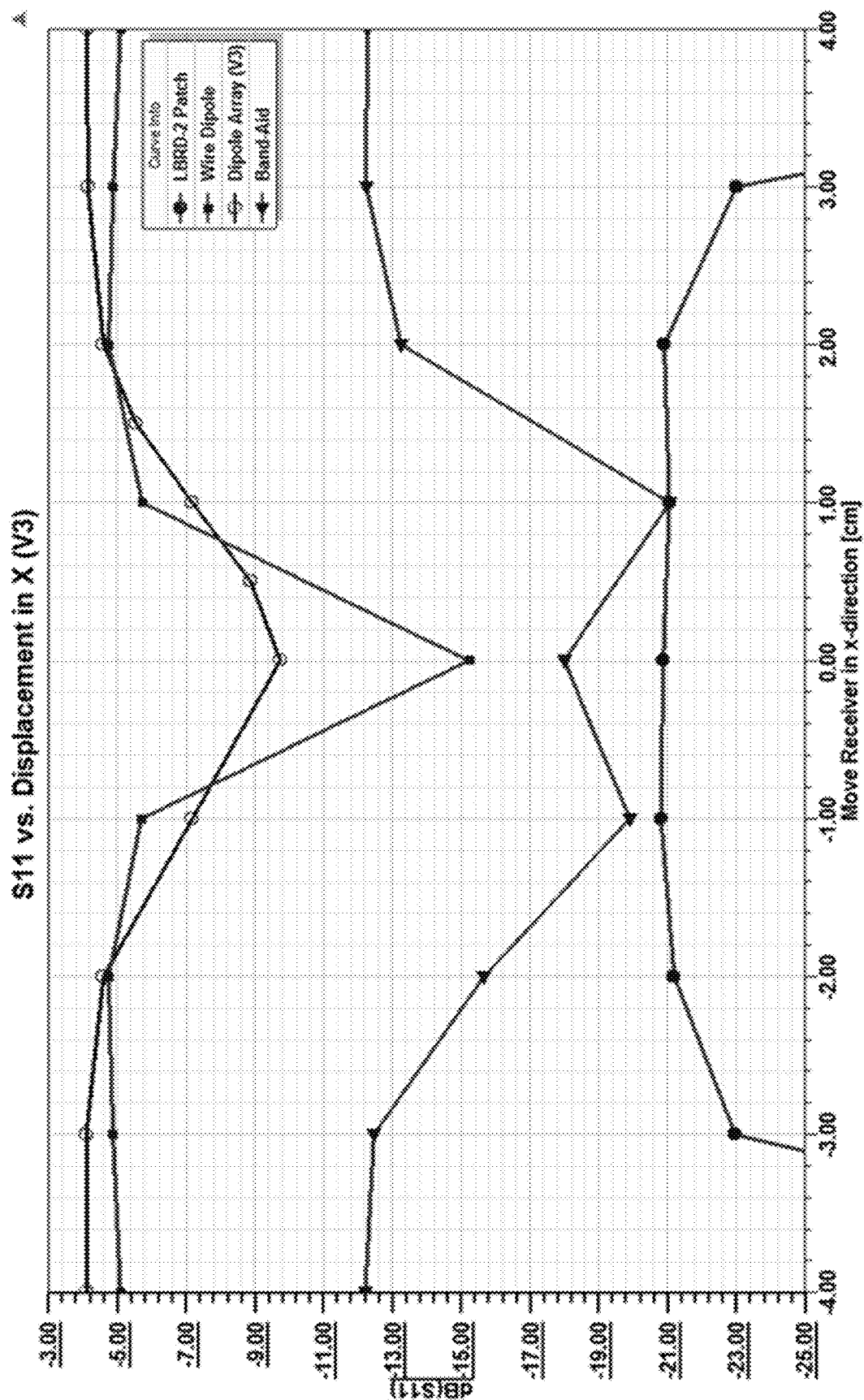

FIGS. 11A to 11C show examples of reflection profiles for a number of antenna designs from FIG. 9. Again, as demonstrated, an array design can be optimized such that reflection from around the intended location(s) of implantable simulator device may be suppressed. The wire dipole, for example, demonstrates a notch in its reflection profile. At the same time, the patch design exhibits a rather flat reflection profile generally 21 dB down. Noteworthy is that the dipole array design version 1 has a reflection profile similar to that from the patch design, although slightly less suppressed at 16 dB or so. In general, the spatial scope of the rejection can be broader for the judicious array design. Specifically, the magnitude of the reflection may be used to match/align the suppression region with the location of the implant. As the implant may be subcutaneously located, knowledge of the region over which the reflection profile remains flat and suppressed may assist in optimally aligning the Tx and Rx antennas, which may enhance efficiency in energy transmission to the implant.

Figure 12A:
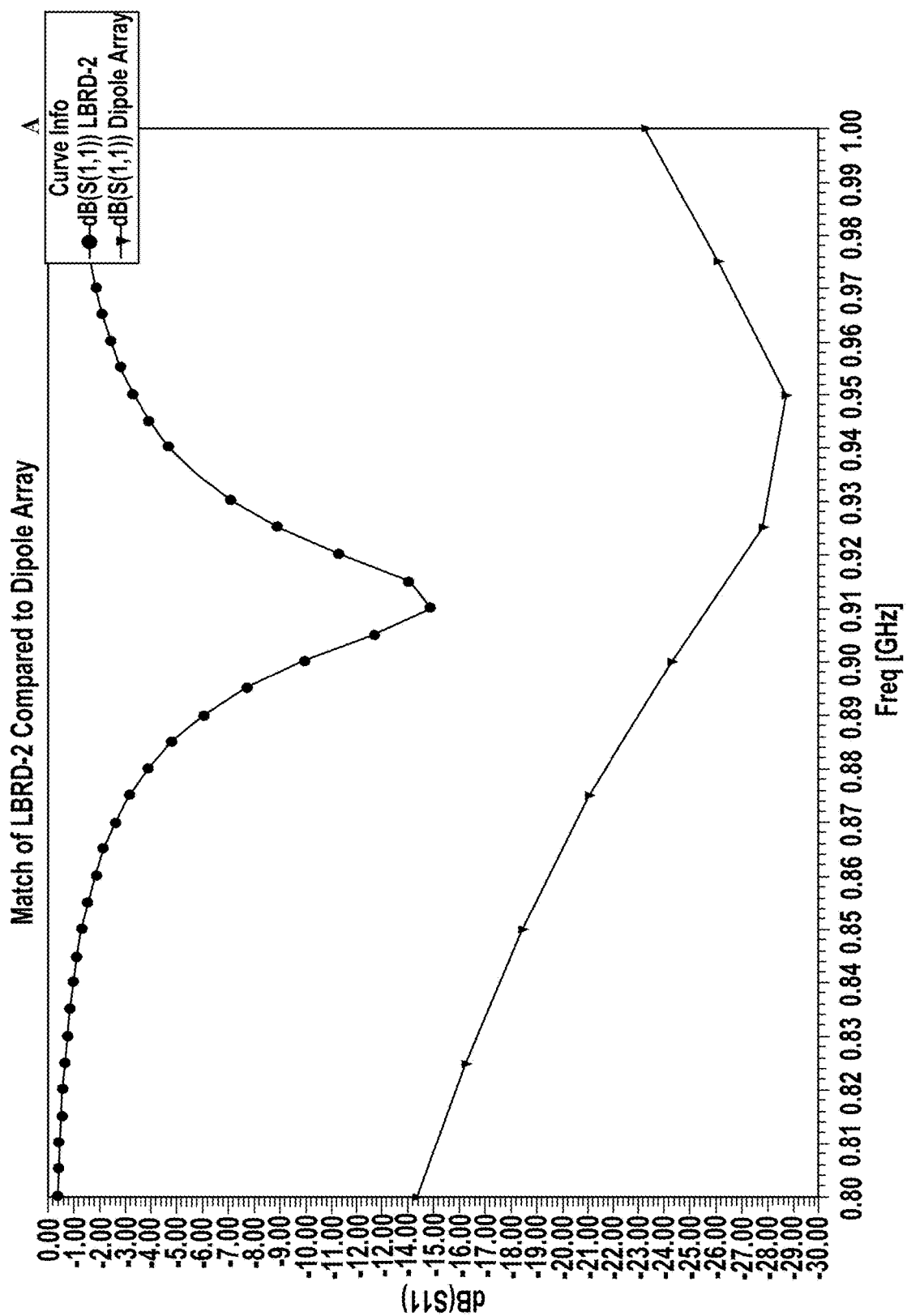
FIGS. 12A and 12B show examples of impedance performance of an antenna design.
Figure 12B:
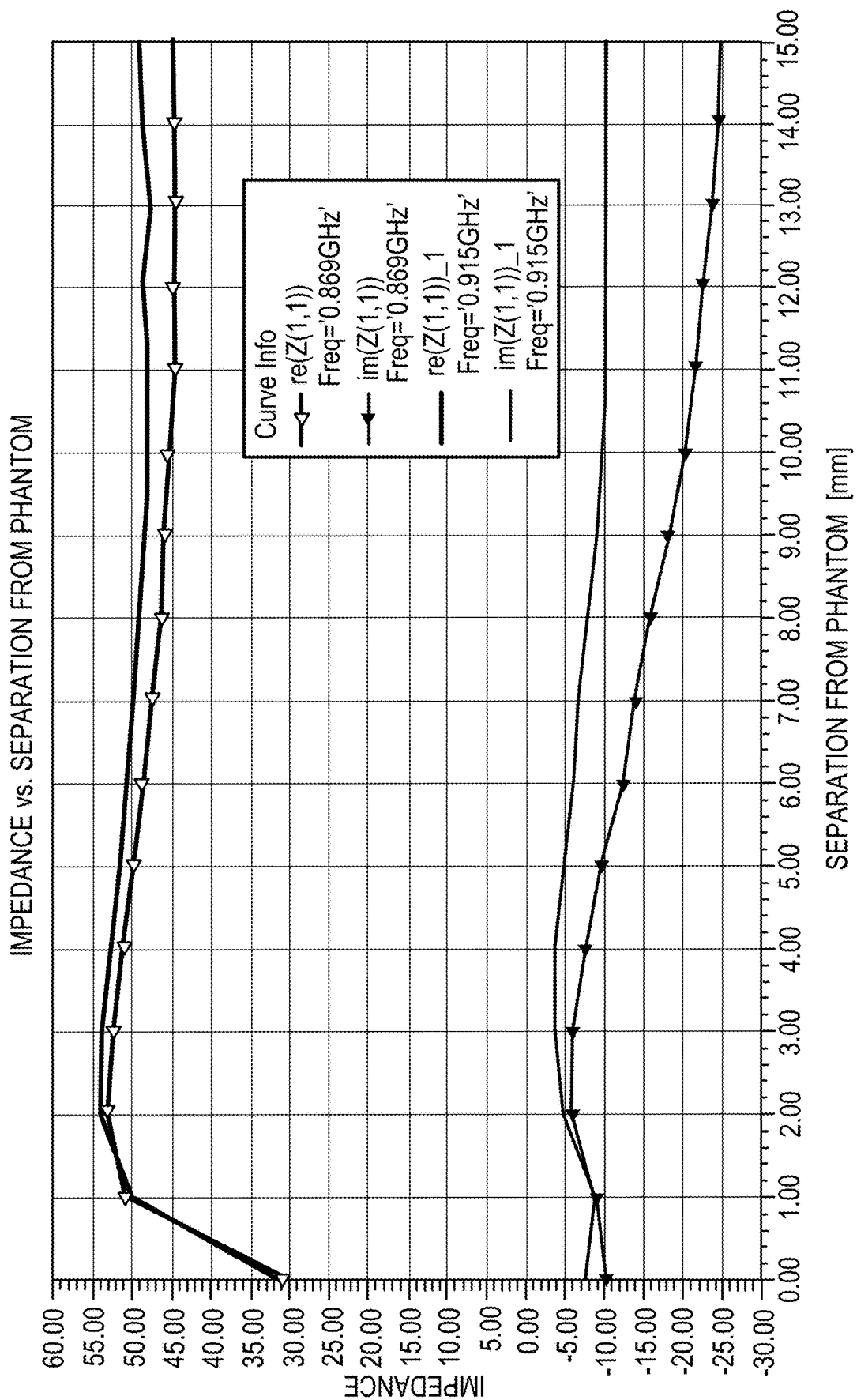
Figure 14D:
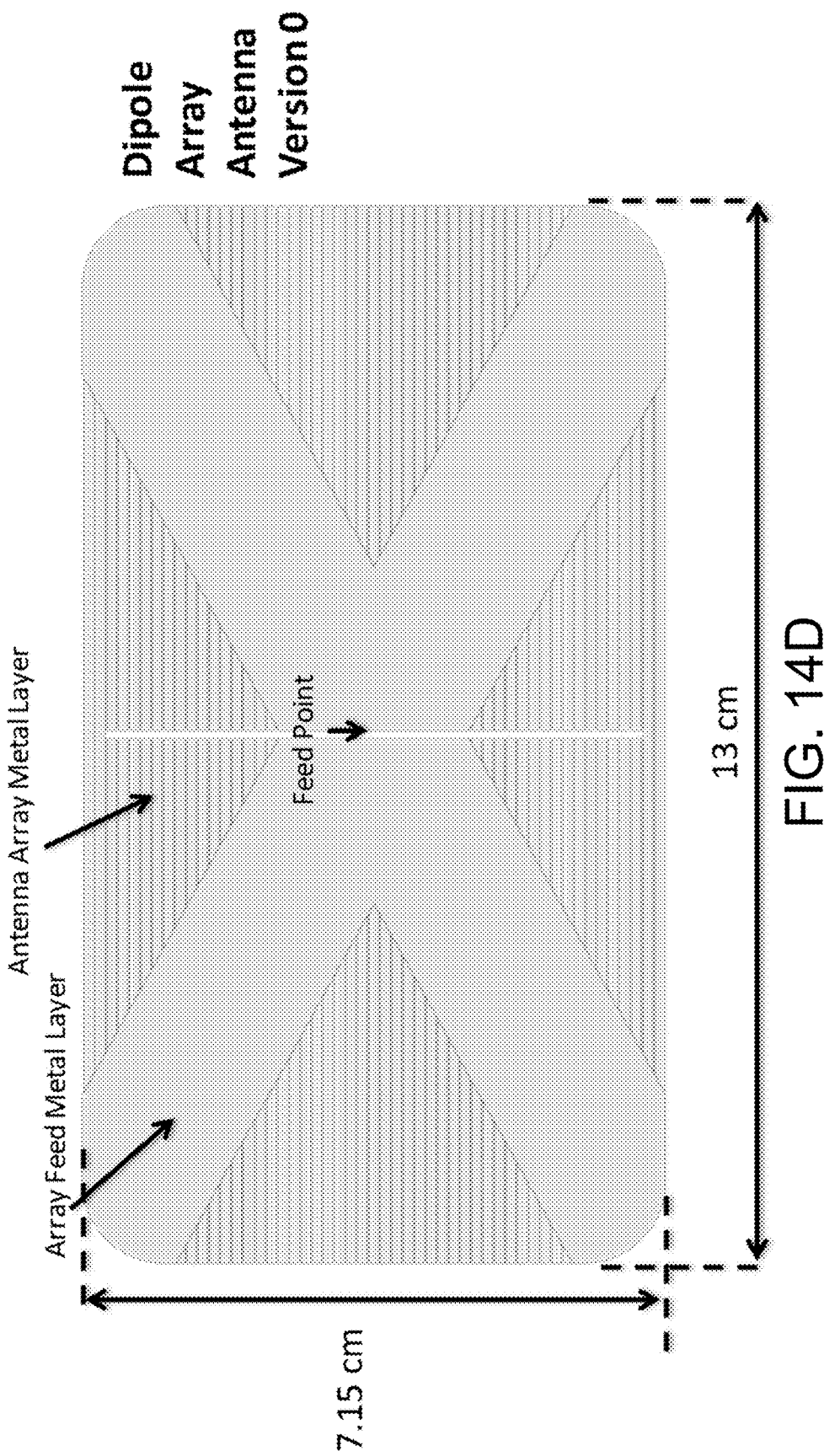

FIGS. 12A and 12B show examples of impedance performance of the antenna design from FIG. 14D. In particular, FIG. 12A shows the antenna match as a function of operating frequency for a baseline patch antenna and the example of an array design of FIG. 14D. The impedance of the array design represents a more superior antenna impedance match over a broader band of the applicable operating spectrum. FIG. 12B shows the impedance of the antenna device when RF energy is transmitted at 869 MHz and 915 MHz into a phantom while separating that antenna from the phantom thereby increasing the air gap. The antenna remains matched in spite of the change of impedance of the medium in front of it. As shown, the array design leads to an apparent impedance more consistently hovering around 50Ω rendering the design advantageous for matching to the impedance of the 50Ω RF source.

Figure 13A:
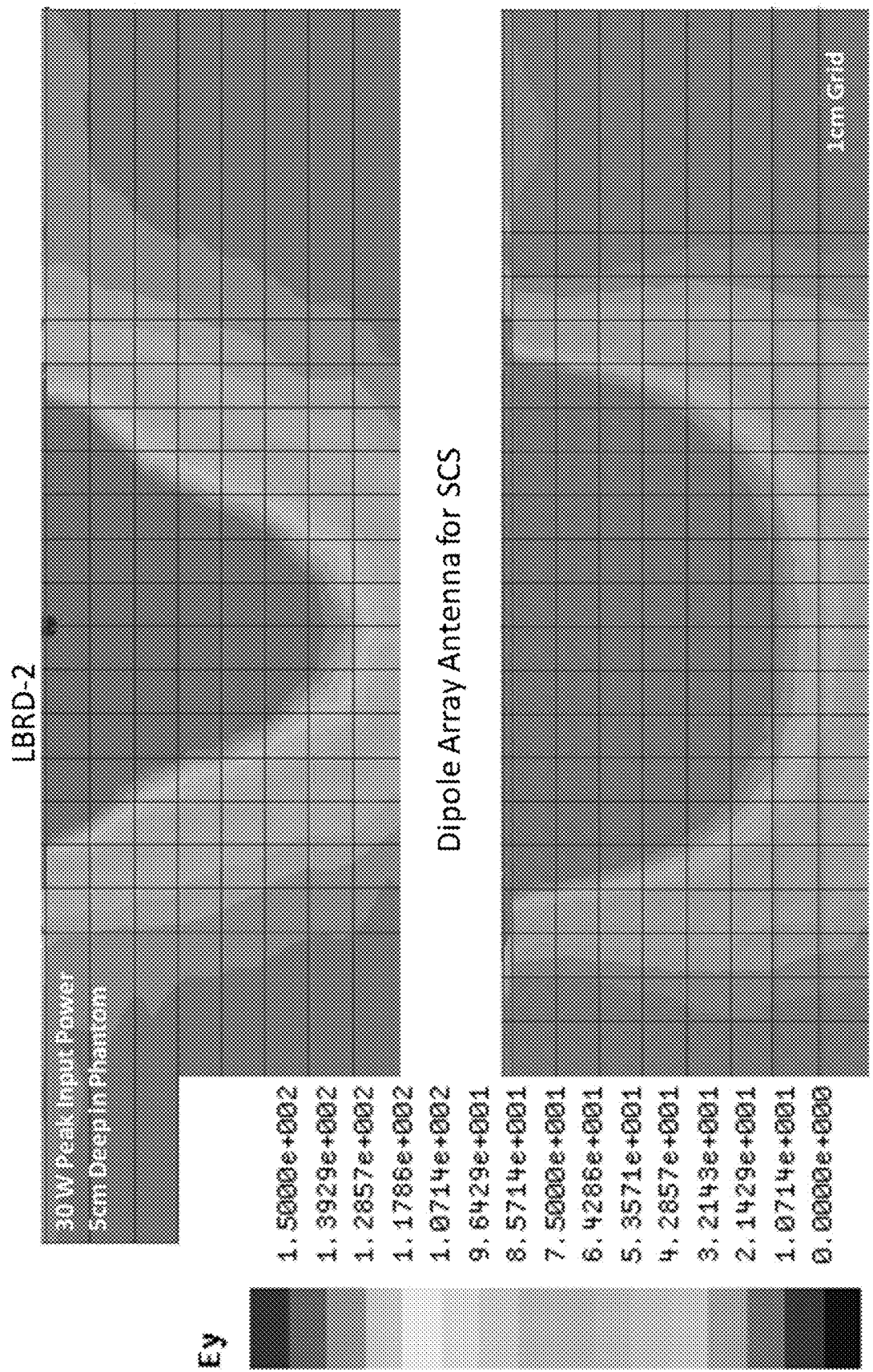
FIGS. 13A to 13C show examples of radiation patterns for some antenna design.
Figure 13B:
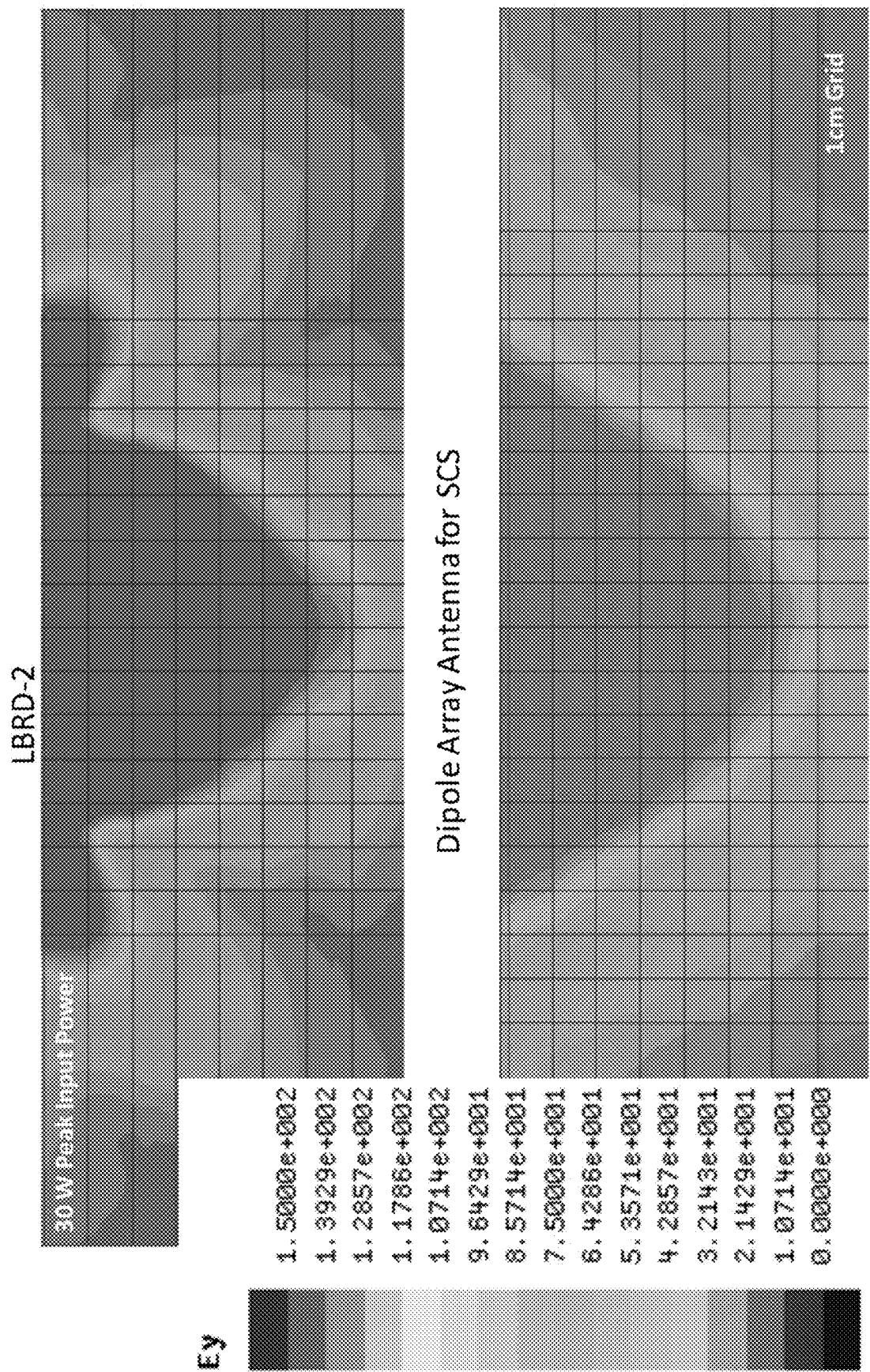
Figure 13C:
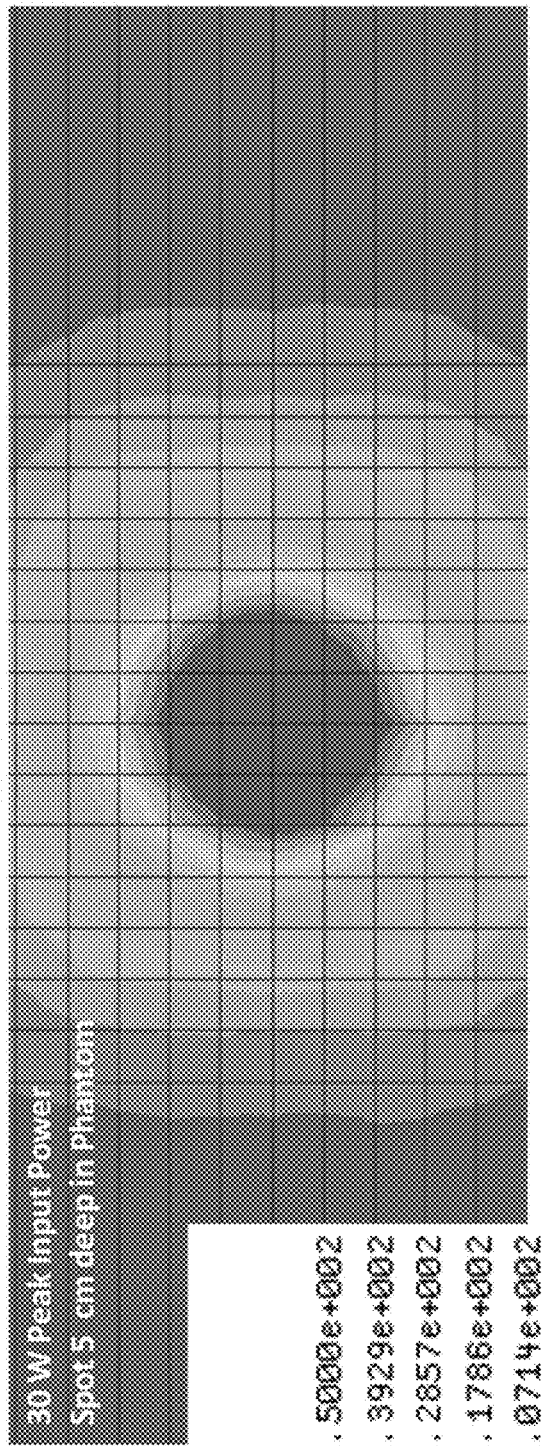
Figure 13C:
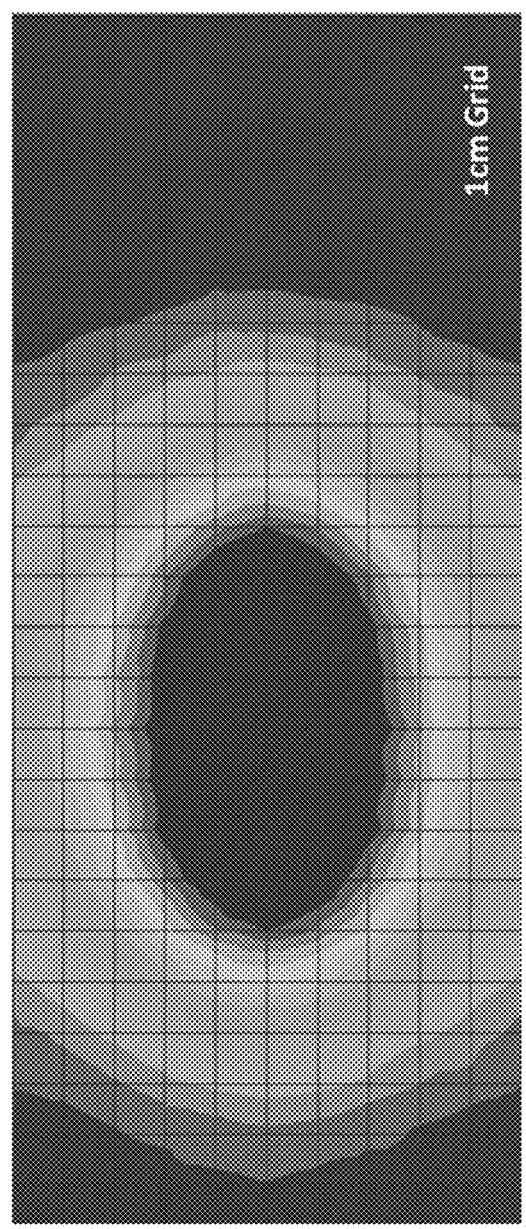

FIGS. 13A to 13C show examples of radiation patterns for the example of antenna designs from FIG. 14D. FIGS. 13A and 13B respectively show input power spatial distribution at vertical planes parallel and perpendicular to the E-field. The input power spatial distributions from the patch antenna (LBRD-2) and dipole array antenna (from FIG. 14D) are compared. FIG. 13C shows the input power spatial distribution at a spot 5 cm deep for a patch antenna (LBRD-2) at the top and a dipole array antenna (from FIG. 14D) at the bottom. The patterns consistently demonstrate the advantageous power deposition feature of the dipole array design in that the dipole array design represents a more uniform power deposition pattern with less directivity characteristics such as side lobes and spikes in deposition patterns.

Figure 14E:
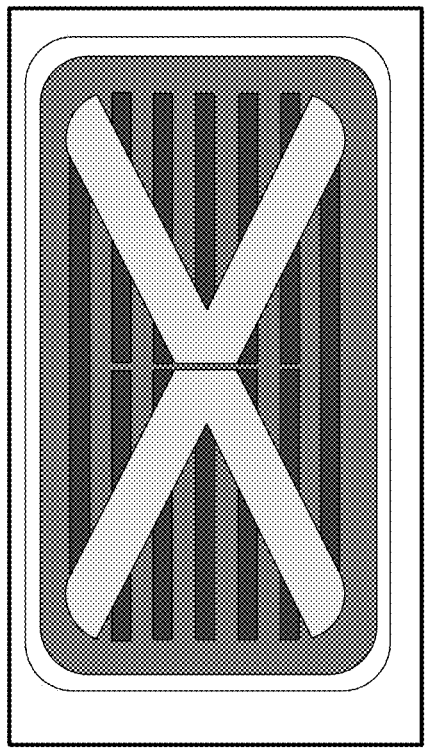
Figure 14E:
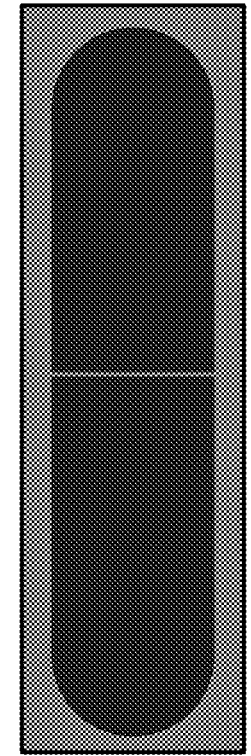
Figure 14E:
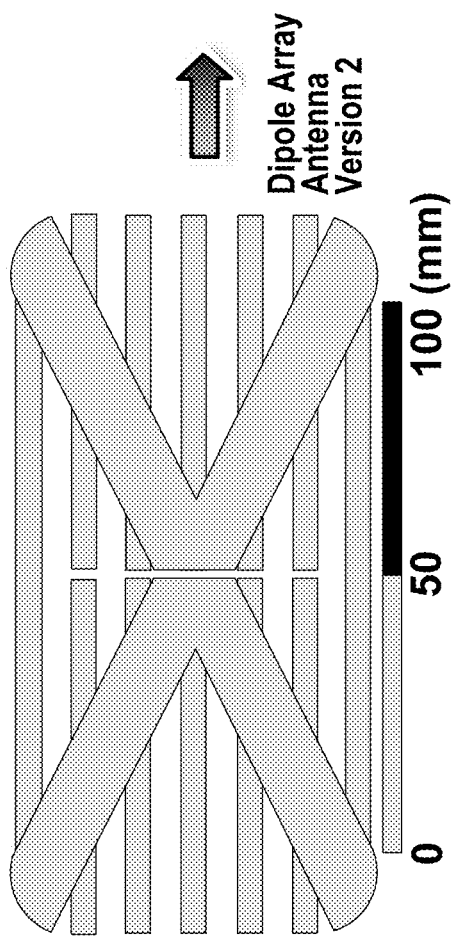
Figure 14E:
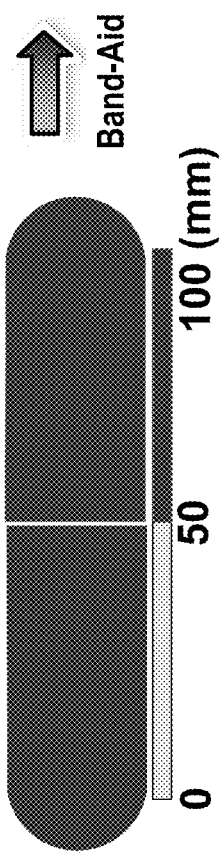
Figure 14F:
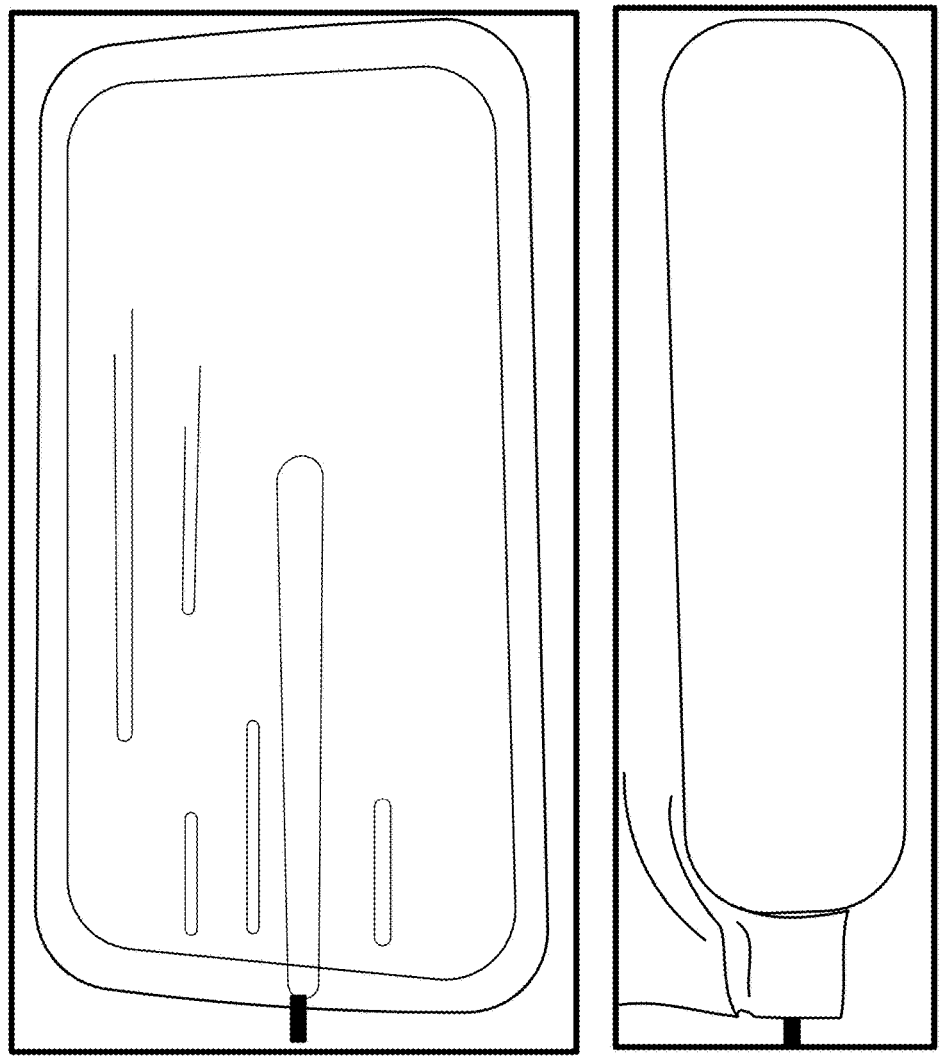
Figure 14G:
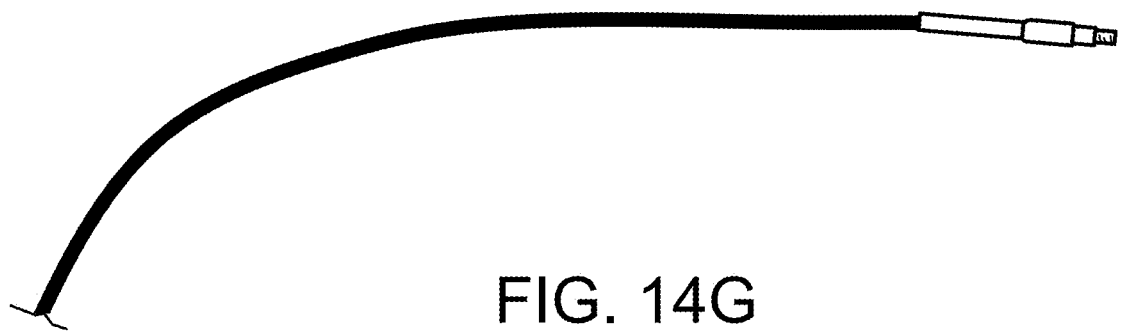

Examples of the implementation of a fabric antenna are shown in FIGS. 14E to 14F. These examples include the dipole array antenna version 2 (shown in FIG. 14D), and the band aid antenna (shown in FIG. 6B and FIG. 4D respectively). Both examples can be implemented as fabric antennas. Dimensions, individual conductor layers, and other details for these implementations are illustrated in FIGS. 14A to 14G. In particular, FIG. 14E shows the outlines of the silver conductive ink after being screen printed onto a thin dielectric substrate, and transferred to a wearable fabric. The silver conductive ink printed trace, may have thickness on the order of 25 microns, and may have elastic properties, such that it can stretch and bend along with the fabric, as the human subject wears the antenna assembly for daily routines. Moreover, the mechanical strength and shape of the fabric antenna, are provided by the fabric that the antenna adheres to. FIG. 14F shows the final wearable fabric antenna prototype of a band aid design with all the fabric layers and the RF feed cable.

The process of manufacturing the antenna may include printing the silver ink trace onto a transfer sheet, via screen printing; and then adding a thin dielectric layer, via screen printing, to prevent any oxidation of the silver ink trace. While this printing step may suffice for a single layer fabric antenna, such as an implementation of the band aid design shown in FIG. 14F, in the case of the dipole array antenna, a second layer of silver conductive ink is printed on top of the dielectric layer, which isolates the two conducive layers.

The silver conductive ink trace and dielectric insulator stack with the transfer sheet are then applied to an elastic fabric, such as, for example, elastic polyurethane material including Lycra. The application may involve a hot press process using, for example, a hot press machine, or any clothing iron. This process step may be very similar to that of applying a typical iron-on patch to clothing. The RF feed cable (e.g., in FIG. 14G) may then be attached to the silver ink conductive layer by applying a conductive epoxy to end of the cable and to the antenna at its feed point. Thereafter a thin 3M adhesive layer may be used to add a top layer of elastic fabric, resulting in a flexible, breathable, conformable fabric antenna that can be embedded in clothing. In this manner, a fabric antenna configuration can be implemented to allow a human patient who has received an implantable stimulator device to engage in daily routines while wearing the antenna assembly. The fabric antenna serves as a non-inductive interface to transmit electric energy wirelessly into the passive implantable stimulator device that does not have a battery. In some cases, the fabric antenna may also wirelessly receive signals, such as telemetry signals, from the implantable stimulator device. The fabric antenna may be part of a microwave field stimulator (MFS) device that is external to the human patient. In some cases, the fabric antenna may be connected to the controller portion of the MFS device.

A number of implementations have been described. Nevertheless, it will be understood that various modifications may be made. Accordingly, other implementations are within the scope of the following claims.

What is claimed is:

1. A wearable antenna comprising:
 a conductive signal layer that includes two or more conductor strips, wherein at least one of the two or more conductor strips is configured to provide a radiating surface;
 a feed conductive layer comprising a feed point; and
 an insulating layer disposed between the conductive signal layer and the feed conductive layer,
 wherein at least one of the conductive signal layer, the feed conductive layer, and the insulating layer incorporates a fabric material,
 wherein the wearable antenna is shaped and sized with sufficient flexibility to be stretched and bent as a subject implanted with a passive implantable stimulator device maintains routine daily activities, and wherein the wearable antenna is electrically tuned and the feed point of the feed conductive layer is connectable to a controller such that when the wearable antenna is worn by the subject, the wearable antenna is non-inductively coupled to the passive implantable stimulator device to supply electrical power to the passive implantable stimulator device wirelessly through the radiating surface.

2. The wearable antenna of claim 1, wherein the two or more conductor strips include a first portion and a second portion, and wherein the first portion and the second portion are arranged substantially in parallel with respect to each other.

3. The wearable antenna of claim 2, wherein at least one of the first portion and the second portion is shaped substantially symmetrically.

4. The wearable antenna of claim 2, wherein the first portion and the second portion are shaped to have at least one round corner.

5. The wearable antenna of claim 1, wherein the radiating surface is oriented to face the subject's skin when the wearable antenna is worn by the subject.

6. The wearable antenna of claim 1, wherein the conductive signal layer comprises conductive ink printed on the fabric material.

7. The wearable antenna of claim 1, wherein the conductive signal layer comprises metal woven into the fabric material.

8. The wearable antenna of claim 1, wherein the insulating layer comprises a fabric layer.

9. The wearable antenna of claim 1, wherein the fabric material is part of a clothing of the subject.

10. The wearable antenna of claim 1, wherein the two or more conductor strips comprise one or more conductor strips each having a gap at substantially a midpoint, and wherein the midpoint divides the conductor strip into substantially symmetric halves.

11. The wearable antenna of claim 1, wherein the feed conductive layer comprises an X-shaped conductor trace having a gap at substantially a midpoint, and wherein the midpoint divides the feed conductive layer into substantially symmetric halves.

12. The wearable antenna of claim 11, wherein the feed conductive layer comprises an X-shaped conductor trace having a central gap that divides the feed conductive layer into substantially symmetric halves.

13. The wearable antenna of claim 12, wherein the feed point is located at the central gap and is connectable to the controller.

14. The wearable antenna of claim 1, wherein the wearable antenna has a power deposition pattern that varies by less than 33% over an implantation depth of 1 cm.

15. The wearable antenna of claim 1, wherein the wearable antenna is tuned and matched throughout a band of operating frequencies that range from a first frequency of about 300 MHz to a second frequency of about 3 GHz.

16. The wearable antenna of claim 1, wherein the wearable antenna comprises a dipole antenna.

17. The wearable antenna of claim 1, wherein the wearable antenna comprises at least one of a patch antenna.

18. A system comprising:
a passive implantable stimulator;
a controller; and
a wearable antenna, the wearable antenna comprising:
a conductive signal layer that includes two or more conductor strips, at least one of which conductor strips is configured to provide a radiating surface;
a feed conductive layer comprising a feed point; and
an insulating layer disposed between the conductive signal layer and the feed conductive layer,
wherein at least one of the conductive signal layer, the feed conductive layer, and the insulating layer incorporates a fabric material,
wherein the wearable antenna is shaped and sized with sufficient flexibility to be stretched and bent as a subject implanted with the passive implantable stimulator device maintains routine daily activities, and
wherein the wearable antenna is electrically tuned and the feed point of the feed conductive layer is connectable to the controller such that when the wearable antenna is worn by the subject, the wearable antenna is non-inductively coupled to the passive implantable stimulator device to supply electrical power to the passive implantable stimulator device wirelessly through the radiating surface.

19. The wearable antenna of claim 18, wherein the conductive signal layer comprises conductive ink printed on the fabric material of the wearable antenna.

20. The wearable antenna of claim 18, wherein the conductive signal layer comprises metal woven into the fabric material of the wearable antenna.

* * * * *